US009217018B2

(12) United States Patent
Onikienko et al.

(10) Patent No.: US 9,217,018 B2
(45) Date of Patent: Dec. 22, 2015

(54) HSP70 FUSION PROTEIN CONJUGATES AND USES THEREOF

(71) Applicants: Sergei B Onikienko, St. Petersburg (RU); Alex Nivorozhkin, West Roxbury, MA (US); Alexander V Zemlyanoi, St. Petersburg (RU); Mikhail Viktorovich Shorokhov, Leningradskay Oblast (RU); Vladimir Ivanovich Pereguda, Leningradskay Oblast (RU); Valery Aleksandrovich Chereshnev, Perm (RU)

(72) Inventors: Sergei B Onikienko, St. Petersburg (RU); Alex Nivorozhkin, West Roxbury, MA (US); Alexander V Zemlyanoi, St. Petersburg (RU); Mikhail Viktorovich Shorokhov, Leningradskay Oblast (RU); Vladimir Ivanovich Pereguda, Leningradskay Oblast (RU); Valery Aleksandrovich Chereshnev, Perm (RU)

( * ) Notice: Subject to any disclaimer, the term of this patent is extended or adjusted under 35 U.S.C. 154(b) by 0 days.

(21) Appl. No.: 13/716,087

(22) Filed: Dec. 15, 2012

(65) Prior Publication Data

US 2013/0156694 A1   Jun. 20, 2013

Related U.S. Application Data

(60) Provisional application No. 61/576,288, filed on Dec. 15, 2011.

(51) Int. Cl.
*C07K 14/47* (2006.01)
*A61K 38/17* (2006.01)

(52) U.S. Cl.
CPC ............ *C07K 14/47* (2013.01); *A61K 38/1709* (2013.01); *C07K 2319/00* (2013.01); *C07K 2319/30* (2013.01); *C07K 2319/50* (2013.01)

(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell |
| 5,624,821 A | 4/1997 | Winter et al. |
| 5,643,575 A | 7/1997 | Martinez et al. |
| 5,648,260 A | 7/1997 | Winter et al. |
| 5,655,517 A | 8/1997 | Coffee |
| 5,914,345 A | 6/1999 | Slepian |
| 5,919,455 A | 7/1999 | Greenwald et al. |
| 5,932,462 A | 8/1999 | Harris et al. |
| 5,985,265 A | 11/1999 | Kinstler et al. |
| 6,194,551 B1 | 2/2001 | Idusogie et al. |
| 6,428,771 B1 | 8/2002 | Steiner et al. |
| 6,444,226 B1 | 9/2002 | Steiner et al. |
| 6,846,845 B2 | 1/2005 | Takahashi |
| 7,052,686 B2 | 5/2006 | Lee et al. |
| 2003/0012793 A1 | 1/2003 | Srivastava |
| 2005/0014934 A1 | 1/2005 | Hintin et al. |

FOREIGN PATENT DOCUMENTS

| | | |
|---|---|---|
| WO | WO 94/29351 | 12/1994 |
| WO | WO 99/51642 | 10/1999 |
| WO | WO 00/42072 | 7/2000 |
| WO | WO 2004/056312 | 7/2004 |
| WO | WO 2007/098500 | 8/2007 |
| WO | WO 2009/155936 | * 12/2009 |
| WO | WO 2010/086418 | 8/2010 |
| WO | WO 2012/008834 | 1/2012 |
| WO | WO 2012/107095 | 8/2012 |

OTHER PUBLICATIONS

Lo et al. High level expression and secretion of Fc-X fusion proteins in mammalian cells. Protein Eng. Jun. 1998;11(6):495-500.*
Pasut et al. Protein, peptide and non-peptide drug PEGylation for therapeutic application. Expert Opin. Ther. Pat. 2004;14(6):859-894.*
Haspel et al. System for cleavable Fc fusion proteins using tobacco etch virus (TEV) protease. Biotechniques. Jan. 2001;30(1):60, 61 and 64-66.*
Akira, Ito et al.: "Antitumor effects of combined therapy of recombinant heat shock protein 70 and hyperthermia using magnetic nanoparticles in an experimenal subcutaneous murine melanoma", Cancer Immunology, Immunotherapy (Jan. 2004) vol. 53, No. 1, pp. 26-32.
Doeppner, Thorsten R et al.: "TAT-HSP70-mediated neuroprotection and increased survival of neuronal precursor cells after focal cerebral ischemia in mice", Journal of Cerebral Blood Flow & Metabolism (Apr. 2009) vol. 29, No. 6, pp. 1187-1196.
Guzhova, Irina et al.: "HSP70 chaperone as a survival factor in cell pathology", International Review of Cytology Elsevier Academic Press, Inc., USA Series: International Review of Cytology-A Survey of Cell Biology (2006) pp. 101-149.
Massa, CH et al.: "Enhanced efficacy of tumor cell vaccines transfected with secretable HSP70", Cancer Research, American Association for Cancer Research, US (Feb. 2004) vol. 64, No. 4, pp. 1502-1508.
Schmidt, SR: "Fusion-proteins as biopharmaceuticals—applications and challenges", Current Opinion in Drug Discovery and Development, Current Drugs, London, Great Britain (Mar. 2009) vol. 12, No. 2, pp. 284-295.
Shevtsov, MA et al.: "HSP70 stress protein is a promising tool in the treatment of brain tumors in children", European Journal of Cancer (Sep. 2011) vol. 47, No. S1, p. S291.
Yamazaki, Koichi et al.: "Cutting Edge: Tumor secreted heat shock-fusion protein elicits CB8 cells for rejection", The Journal Immunology, The American Association of Immunologists, US (Jan. 1999) vol. 163, No. 10, pp. 5178-5182.
Atochin DN et al.: "The Phosphorylation State of eNOS Modulates Vascular Reactivity and Outcome of Cerebral Ischemia in vivo." Journal of Clinical Investigation (2007) 117:1961.
Chamow Steven M. et al.: Modification of CD4 Immunoadhesin with Monomethoxypoly(Ethylene Glycol) Aldehyde via Reductive Alkylation in Bioconjugate Chem., 1994, 5 (2), pp. 133-140.

(Continued)

*Primary Examiner* — David Romeo
(74) *Attorney, Agent, or Firm* — JWIP & Patent Services, LLC; Jacob G. Weintraub, Esq.

(57) ABSTRACT

The present invention relates to novel therapies that utilize HSP70 fusion proteins for the treatment of disorders or conditions regulated by HSP70.

8 Claims, 5 Drawing Sheets

(56) References Cited

OTHER PUBLICATIONS

Ciocca, DR and Calderwood SK: "Heat Shock Proteins in Cancer : Diagnostic, Prognostic, Predictive, and Treatment Implications. Cell Stress and Chaperone." (2005) 10(2):86-103.

Duncan AR and Winter G.: "The Binding Site for Clq on IgG." Nature (1988) 332:738-740.

Ekimova, Irina V. et al.: "Exonenous Protein Hsp70/Hsc70 can Penetrate into Brain Structures and Attenuate the Severity of Chemically-Induced Seizures." J. Neurochem. (2010) 115:1035-1044.

Gehrig SM et al.: "Hsp72 preserves muscle function and slows progression of severe muscular dystrophy." Nature (2012) 4847394:394-8.

Gifondorwa David J. et al.: Exogenous Delivery of Heat Shock Protein 70 Increases Lifespan in a Mouse Model of Amyotrophic Lateral Sclerosis, Journal of Neuroscience, vol. 27, No. 48 (200711-28), pp. 13173-13180.

Guzhova IV et al.: "Review: Hsp70 Chaperone and the Prospects of its application in anticancer therapy." Tsitologiia (2005) 47(3):187-99. [Only—Abstract in English].

Guyer RL et al.: "Immunologlobin Binding by Mouse Intestinal Epithalial Cell Receptors." Journ. Immunol. (1976) 117:587-593.

Hunt C and Morimoto RI: "Conserved Features of Eukaryotic Hsp70 Genes Revealed by Comparison with the Nacleotide Sequence of Human Hsp70 Comparison with the Nucleotide Sequence of Human Hsp70" Proc. Natl. Acad. Sci. U.S.A. (1995) 82:6455-6459.

Idusogie EE et al.: "Mapping of the Clq Binding Site on Rituxan, a Chimeric Antibody with a Human IgG1 Fc." Journ. Immunol. (2000) 164:4178-4184.

Karkkainen AM, et al.: "Vascular Endothelial Growth Factor-D transgenic Mice Show Enhanced Blood Capillary Density, Improved Postischemic Muscle Regeneration, and Increased Susceptibility to Tumor Formation." Blood (2009) 113:4468-4475.

Knowlton et al.: "Heat-Shock Factor-1, Steriod Hormones, and Regulation of Heat-Shock Protein Expression in the Heart." Am. J. Physiol. Heart Cir. Physiol. (2001) 280:H455-H464.

Kustanova G.A. et al.: "Exogenous Heat Shock Protein 70 Mediates Sepis Manifestations and Decreases the M ortality Rate in Rats. Cell Stress and Chaperones." (2006) 11(3):276-286.

Jammes Y et al.: "Chronic Fatigue Syndrome Combines Increased Exercise-Induced Oxidative Stress and Reduced Cytokine and HSP Responses." J. Intern. Med. (2009) 2662:196-206.

Lee CE et al.: "The role of Hormones, Cytokines and Heat Shock Proteins during Age-Related Muscle Loss." Clin. Nutr. 2007, 265:524-34.

Lee J. et al: "Controlled delivery of heat shock protein using an injectable microsphere/hydrogel combination system for the treatment of myocardial infarction", Journal of Controlled Release, Elsevier, Amsterdam, NL, vol. 137, No. 3, Aug. 4, 2009, pp. 196-202.20.

Levin L.A.: Retinal Ganglion Cells and Neuroprotection for Glaucoma, Survey of Ophthalmology, vol. 48, Issue 2, Supplement, Apr. 2003, pp. S21-S24.

Maglara A.A. et al.: "Damage to Developing Mouse Skeletal Muscle Myotubes in Culture: Protective Effect of Heat Shock Proteins." J. Physiol. (2003) 548(3)837-846.

Messina S et al.: "VEGF Overexpression via Adeno-Associated Virus Gene Transfer Promotes Skeletal Muscle Regeneration and Enhances Muscle Function in mdx Mice." FASEB J. (2007) 21:3737-3746.

McConnell K.W. et al: The Role of Heat Shock Protein 70 in Mediating Age-Dependent Mortality in Sepsis. The Journal of Immunology (2011) 186:3718.

Morton JP, Kayani AC, McArdle A, Drust B, Exercise-Induced Stress Response of Skeletal Muscle, with Specific Emphasis on Humans. Sport Med. 2009, 39(8), 643-662.

Nemoto TK et al.: "Disulfide Bridge Mediated at Cysteine 574 is Formed in the Dimer of the 70-kDa Heat Shock Protein." J. Biochem. (2006) 139:677-687.

Panossian A and Wikman G.: Evidence-Based Efficacy of Adaptogens in Fatigue, and Molecular Mechanisms Related to Their Stress-Protective Activity. Curr. Clin. Pharmacol. 2009,4(3)198-219.

Shao et al.: 125I-Labeled Gold Nanorods for Targeted Imaging of Inflammation. ACS Nano (2011) 5(11):8967-8973.

Shields RI et al.: "High Resolution Mapping of the Binding Site on Human IgG1 for FcγRl, FcγRll, FcγRlll, and FcRn and Design of IgG1 Variants with Improved Binding to the FcγR." The Journal of Biological Chemistry (2001) 276 (9):6591-6604.

Shiota M et al.: "Heat Shock Cognate Protein 70 is Essential for Akt Signaling in Endothelial Function," Arterioscler. Thromb. Vasc. Biol. (2010) 30:491-497.

Silva EA et al.: "Spatiotemporal Control of Vascular Endothelial Growth Factor Delivery from Injectable Hydrogels Enhances Angiogenesis." J. Thromb Haemost (2007) 5:590-598.

Turturici G et al.: "HSP 70 and its Molecular Role in Nervous System Diseases, Biochemistry Research International." (Jan. 3, 2011) vol. 2011, Article ID 618127, 18 pages.

Vigh L et al.: "Bimoclomol: a Nontoxic, Hydroxylamine Derivative with Stress Protein-Inducing Activity and Cytoprotective Effect. Nature Medicine." (1997) 3(10):1150-1154.

Vinokurov M. et al.: "Recombinant Human Hsp70 Protects Against Lipoteichoic Acid-Induced Imflammation Manifestations at the Cellular and Organismal Levels, Cell Stress and Chaperones: A Comprehensive Journal of Stress Biology and Medicine." Springer Netherlands, Dordrecht (2008) 17(1):89-101.

Wagers AJ and Conboy IM: "Cellular and Molecular Signatures of Muscle Regeneration: Current Concepts and Controversies in Adult Myogenesis" Cell (2005) 122:659-667.

Whitham M. and Fortes M.B.: Heat Shock Protein 72: Release and Biological Significance During Exercise, Frontiers in Bioscience (2008) 13:1328-1339.

O'Brien, Melanie C. et al.: "Lysine 71 of the chaperone protein Hsc70 is essential for ATP hydrolysis", The Journal of Biological Chemistry (Jul. 1996) vol. 271, No. 27, pp. 15874-15878.

Jinwal, Umesh K. et al.: "Chemical manipulation of Hsp70 ATPase activity regulates tau stability", The Journal of Neuroscience (Sep. 2009) vol. 29, No. 39, pp. 12079-12088.

Agranovsky, Alexey A. et al.: "The beet yellows closterovirus p65 homologue of HSP70 chaperones has ATPase activity associated with its conserved N-terminal domain but does not interact with unfolded protein chains", Journal of General Virology (1997) vol. 78, pp. 535-542.

* cited by examiner

SEQUENCE LISTING

<160> NUMBER OF SEQ ID NOS: 2

<210> SEQ ID NO 1
<211> LENGTH: 883
<212> TYPE: PRT

<213> ORGANISM: Artificial Sequence
<220> FEATURE:
<223> OTHER INFORMATION: Synthetic Sequence

<400> SEQUENCE: 1

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
        100                 105                 110

Thr Ile Ser Lys Ala Lys Gly Gln Pro Arg Glu Pro Gln Val Tyr Thr
    115                 120                 125

Leu Pro Pro Ser Arg Asp Glu Leu Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
    210                 215                 220

Lys Ala Ser Gly Ala Gly Ser Thr Thr Glu Asn Leu Tyr Phe Gln Gly
225                 230                 235                 240

Gly Ser Met Ala Lys Ala Ala Ile Gly Ile Asp Leu Gly Thr Thr
                245                 250                 255

Tyr Ser Cys Val Gly Val Phe Gln His Gly Lys Val Glu Ile Ile Ala
            260                 265                 270

Asn Asp Gln Gly Asn Arg Thr Thr Pro Ser Tyr Val Ala Phe Thr Asp
        275                 280                 285

Thr Glu Arg Leu Ile Gly Asp Ala Ala Lys Asn Gln Val Ala Leu Asn
    290                 295                 300

Pro Gln Asn Thr Val Phe Asp Ala Lys Arg Leu Ile Gly Arg Lys Phe
305                 310                 315                 320

Gly Asp Pro Val Val Gln Ser Asp Met Lys His Trp Pro Phe Gln Val
                325                 330                 335

Ile Asn Asp Gly Asp Lys Pro Lys Val Gln Val Ser Tyr Lys Gly Asp
            340                 345                 350

Thr Lys Ala Phe Tyr Pro Glu Glu Ile Ser Ser Met Val Leu Thr Lys
        355                 360                 365

Met Lys Glu Ile Ala Glu Ala Tyr Leu Gly Tyr Pro Val Thr Asn Ala
    370                 375                 380

Val Ile Thr Val Pro Ala Tyr Phe Asn Asp Ser Gln Arg Gln Ala Thr
```

```
            385                 390                 395                 400
Lys Asp Ala Gly Val Ile Ala Gly Leu Asn Val Leu Arg Ile Ile Asn
                    405                 410                 415

Glu Pro Thr Ala Ala Ile Ala Tyr Gly Leu Asp Arg Thr Gly Lys
                420                 425                 430

Gly Glu Arg Asn Val Leu Ile Phe Asp Leu Gly Gly Gly Thr Phe Asp
                    435                 440                 445

Val Ser Ile Leu Thr Ile Asp Asp Gly Ile Phe Glu Val Lys Ala Thr
                450                 455                 460

Ala Gly Asp Thr His Leu Gly Gly Glu Asp Phe Asp Asn Arg Leu Val
465                 470                 475                 480

Asn His Phe Val Glu Glu Phe Lys Arg Lys His Lys Lys Asp Ile Ser
                    485                 490                 495

Gln Asn Lys Arg Ala Val Arg Arg Leu Arg Thr Ala Cys Glu Arg Ala
                500                 505                 510

Lys Arg Thr Leu Ser Ser Ser Thr Gln Ala Ser Leu Glu Ile Asp Ser
                515                 520                 525

Leu Phe Glu Gly Ile Asp Phe Tyr Thr Ser Ile Thr Arg Ala Arg Phe
530                 535                 540

Glu Glu Leu Cys Ser Asp Leu Phe Arg Ser Thr Leu Glu Pro Val Glu
545                 550                 555                 560

Lys Ala Leu Arg Asp Ala Lys Leu Asp Lys Ala Gln Ile His Asp Leu
                565                 570                 575

Val Leu Val Gly Gly Ser Thr Arg Ile Pro Lys Val Gln Lys Leu Leu
                580                 585                 590

Gln Asp Phe Phe Asn Gly Arg Asp Leu Asn Lys Ser Ile Asn Pro Asp
                595                 600                 605

Glu Ala Val Ala Tyr Gly Ala Ala Val Gln Ala Ala Ile Leu Met Gly
                610                 615                 620

Asp Lys Ser Glu Asn Val Gln Asp Leu Leu Leu Leu Asp Val Ala Pro
625                 630                 635                 640

Leu Ser Leu Gly Leu Glu Thr Ala Gly Gly Val Met Thr Ala Leu Ile
                645                 650                 655

Lys Arg Asn Ser Thr Ile Pro Thr Lys Gln Thr Gln Ile Phe Thr Thr
                660                 665                 670

Tyr Ser Asp Asn Gln Pro Gly Val Leu Ile Gln Val Tyr Glu Gly Glu
                675                 680                 685

Arg Ala Met Thr Lys Asp Asn Asn Leu Leu Gly Arg Phe Glu Leu Ser
                690                 695                 700

Gly Ile Pro Pro Ala Pro Arg Gly Val Pro Gln Ile Glu Val Thr Phe
705                 710                 715                 720

Asp Ile Asp Ala Asn Gly Ile Leu Asn Val Thr Ala Thr Asp Lys Ser
                    725                 730                 735

Thr Gly Lys Ala Asn Lys Ile Thr Ile Thr Asn Asp Lys Gly Arg Leu
                740                 745                 750

Ser Lys Glu Glu Ile Glu Arg Met Val Gln Glu Ala Glu Lys Tyr Lys
                755                 760                 765

Ala Glu Asp Glu Val Gln Arg Glu Arg Val Ser Ala Lys Asn Ala Leu
                770                 775                 780

Glu Ser Tyr Ala Phe Asn Met Lys Ser Ala Val Glu Asp Glu Gly Leu
785                 790                 795                 800

Lys Gly Lys Ile Ser Glu Ala Asp Lys Lys Lys Val Leu Asp Lys Cys
                805                 810                 815
```

```
Gln Glu Val Ile Ser Trp Leu Asp Ala Asn Thr Leu Ala Glu Lys Asp
                820                 825                 830
Glu Phe Glu His Lys Arg Lys Glu Leu Glu Gln Val Cys Asn Pro Ile
            835                 840                 845
Ile Ser Gly Leu Tyr Gln Gly Ala Gly Gly Pro Gly Pro Gly Gly Phe
        850                 855                 860
Gly Ala Gln Gly Pro Lys Gly Gly Ser Gly Ser Gly Pro Thr Ile Glu
865                 870                 875                 880
Glu Val Asp

<210> SEQ ID NO 2
<211> LENGTH: 225
<212> TYPE: PRT
<213> ORGANISM: Artificial Sequence
<220> FEATURE:
<223> OTHER INFORMATION: Synthetic Sequence

<400> SEQUENCE: 2

Thr His Thr Cys Pro Pro Cys Pro Ala Pro Glu Leu Leu Gly Gly Pro
1               5                   10                  15
Ser Val Phe Leu Phe Pro Pro Lys Pro Lys Asp Thr Leu Met Ile Ser
            20                  25                  30
Arg Thr Pro Glu Val Thr Cys Val Val Val Asp Val Ser His Glu Asp
        35                  40                  45
Pro Glu Val Lys Phe Asn Trp Tyr Val Asp Gly Val Glu Val His Asn
    50                  55                  60
Ala Lys Thr Lys Pro Arg Glu Glu Gln Tyr Asn Ser Thr Tyr Arg Val
65                  70                  75                  80
Val Ser Val Leu Thr Val Leu His Gln Asp Trp Leu Asn Gly Lys Glu
                85                  90                  95
Tyr Lys Cys Lys Val Ser Asn Lys Ala Leu Pro Val Pro Ile Glu Lys
            100                 105                 110
Thr Ile Ser Lys Ala Lys Gly Gln Pro Arg Glu Pro Gln Val Tyr Thr
        115                 120                 125
Leu Pro Pro Ser Arg Glu Glu Met Thr Lys Asn Gln Val Ser Leu Thr
    130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Pro Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
    210                 215                 220
Lys
225
```

HSP70 FUSION PROTEIN CONJUGATES AND USES THEREOF

RELATED APPLICATIONS

This application is a PCT application that claims the benefit of priority from U.S. Provisional Patent Application No. 61/576,288, filed on Dec. 15, 2011, the entirety of which is incorporated herein by reference.

BACKGROUND OF THE INVENTION

Heat shock protein 70 (HSP70), one of several proteins in the general class of heat shock proteins (HSPs), has been implicated in many processes including folding and unfolding of nascent proteins, activation of a multi-enzymatic complex, and protein transport. Additionally, HSPs are important for the maintenance of cell integrity during normal growth as well as during pathophysiological conditions (Vigh et al. 1997). It has been shown that tissue injury, whether caused by surgery, trauma or disease, results in the induction of heat shock/stress proteins. An inducible form of the 70 kDa heat shock protein family HSP72 has been detected intra- and extra-cellularly in different organs, including skeletal muscles in response to exercise.

The biological significance of these processes appears to be related: to aid cell survival and chaperone misfolded and denatured proteins. As molecular chaperones, HSPs are also fundamental in facilitating cellular remodeling processes inherent to the training response (Morton et al. 2009; Whitman et al. 2008). Moreover, the beneficial effects of HSPs have been implicated in a number of different diseases such as diabetes; wound healing (Atalay et al. Curr. Pep. Prot. Sc. 2009; 10:85); cancer (Ciocca et al., Stress Cell Chap. 2005; 10:86; Guzhova et al. Tsitologia 2005, 47:187); sepsis (McConnell et al.; J. Immun. 2011; 186:3718; Kustanova et al. Cell Stress Chap. 2006; 11:276); cardiac injury (Knowlton et al. Am. J. Physiol. Heart Cir. Physiol. 2001; 280:H455); muscular injury and degeneration; recovery from physical and exercise stress (Morton et al. Sports Med. 2009; 39(8):643); neuro-degeneration including Parkinson disease, Alzheimer disease, Huntington disease, amyotrophic lateral sclerosis (Turturici et al., Biochem. Res. Int. 2011); spinal cord injury (Reddy et al. Neurosurg. Focus 2008, 25(5):1); traumatic brain injury; stroke; eye neurodegenerative diseases including glaucoma and macular degeneration (Levin, Surv. Ophthalm. 2003; 48:S21); and epilepsy (Ekimova et al. J. Neurochem. 2010; 115:1035).

At the same time, it has been found that patients with chronic fatigue syndrome (CFS) present an accentuated exercise-induced oxidative stress. Compared with controls, resting CFS patients had low levels of HSP70 and delayed and marked reduction of HSP70 levels in response to maximal exercise (Jammes et al. 2009). In this regard, HSP70 has been implied as a main mediator of the phytoadaptogens such as *Rhodiola rosea* and *Eleutheroccoccus senticosus* that improve attention, cognitive function and mental performance in fatigue and chronic fatigue syndrome as well as increase endurance. HSP70 inhibits the expression of the NO synthase II and affects the levels of circulating cortisol via direct interaction with glucocorticoid receptors and JNK pathway. Consequently, prevention of the stress-induced NO and associated decrease in ATP production result in increased performance and endurance (Panossian et al. 2009).

In effort to capitalize on the involvement of HSP70 in many of these disorders or conditions, several patent applications have reported the utility of HSPs in relation to the recovery from injury (Slepian, U.S. Pat. No. 5,914,345; Srivastava, US Patent Application US 2003/0012793). Additional applications have focused on compounds that induce HSP70, such as geranylgeranylacetone, which have been described to protect subjects from the effect of ischemic-reperfusion injury (Takahashi N, U.S. Pat. No. 6,846,845 B2).

Although evidence has suggested the role of HSP70 in certain indications, current treatments that have adopted strategies to control in vivo HSP70 production have not met the need in this arena. Moreover, the use of exogenous HSP70 has been limited in application due to issues of low stability. As such, there is strong need for novel therapies that address this current demand.

SUMMARY OF THE INVENTION

Accordingly, the present invention relates to novel therapies that utilize HSP70 for the treatment of disorders or conditions regulated by HSP70 through administration of exogenous HSP70 as an HSP70 fusion protein. In this regard, the present invention provides novel fusion proteins and related formulations of HSP70 that offer therapeutic effectiveness in the treatment of HSP70 related disorders or conditions. Furthermore, the present invention is directed to methods comprising the administration of these HSP70 fusion proteins for use in the treatment of HSP70 related disorders or conditions, for example, for stroke, cancer, or for increased performance capability, e.g., physical and mental, increased endurance, or alleviating fatigue syndrome.

Thus, in one aspect, the invention provides an HSP70 fusion protein comprising (i) a first HSP70 domain fused to (ii) a second Fc domain, wherein the first and second domains are optionally linked by a third linker domain.

In another aspect, the invention provides a pharmaceutical composition comprising an HSP70 fusion protein, wherein the HSP70 fusion protein comprises (i) a first HSP70 domain fused to (ii) a second Fc domain, wherein the first and second domains are optionally linked by a third linker domain, and pharmaceutically acceptable carrier.

In another aspect, the present invention provides a method of treatment of an HSP70 related disorder or condition. The method comprises administering to a subject a therapeutically effective amount of HSP70 fusion protein, and wherein the HSP70 fusion protein comprises (i) a first HSP70 domain fused to (ii) a second Fc domain, wherein the first and second domains are optionally linked by a third linker domain, such that the HSP70 related disorder or condition is treated in the subject.

An additional aspect of the invention provides a method to increase performance, alleviate fatigue syndrome, or treat muscle damage or muscle degeneration. The method comprises administering to a mammal a therapeutically effective amount of HSP70 fusion protein, and wherein the HSP70 fusion protein comprises (i) a first HSP70 domain fused to (ii) a second Fc domain, wherein the first and second domains are optionally linked by a third linker domain, such that performance is increased, the fatigue syndrome is alleviated, or the muscle damage or muscle degeneration is treated in the mammal.

In yet another aspect, the invention provides a method of radioimmunotherapy. The method comprises administering to a subject a therapeutically effective amount of HSP70 fusion protein, wherein the HSP70 fusion protein comprises (i) a first HSP70 domain fused to (ii) a second Fc domain, wherein the first and second domains are optionally linked by a third linker domain, and wherein the HSP70 fusion protein is labeled with one or more radioactive isotopes, such that cancer is treated in the subject.

DETAILED DESCRIPTION OF THE INVENTION

Figure 1:
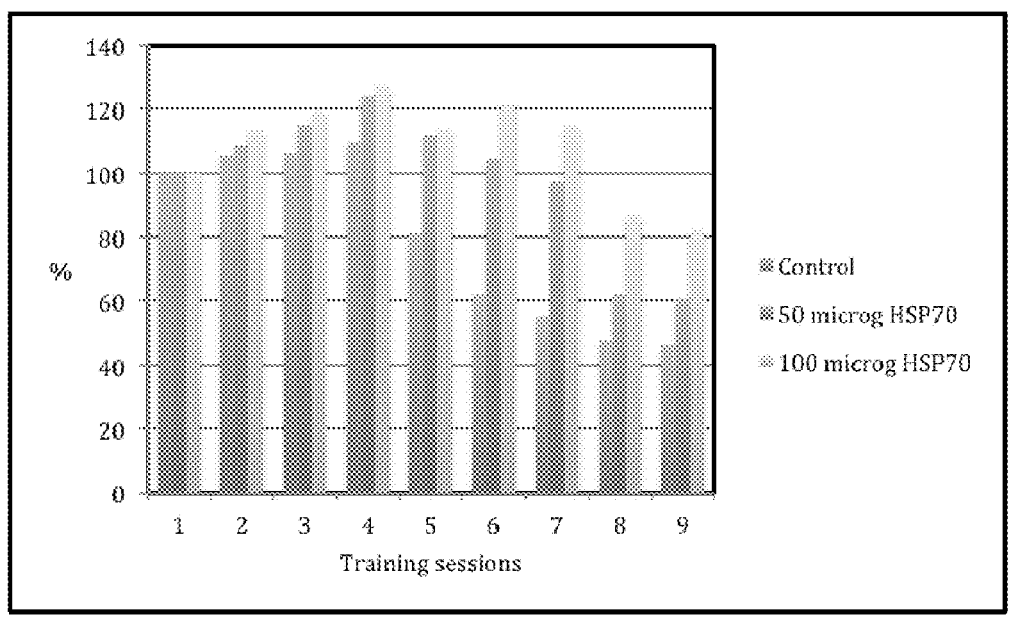
FIG. 1 depicts the variations in endurance (time of exercise to exhaustion) relative to the result of the first exercise session.

Although fusion proteins have been shown in rare occasion to confer beneficial effects upon a therapeutic agent, it is by no means a predictable occurrence, nor is it guaranteed that the fusion protein will have any activity at all. While the selection of the fusion pairing is significant, there are numerous additional unpredictable factors that affect the ability to produce active fusion proteins. This is particularly true when fusing a protein in a position that is highly regarded as one with prominent effect on the activity of the protein, e.g., in folding or binding. As such, the activity of the HSP70 N-terminus and C-terminus derivatives described herein are particularly unexpected, wherein it is well known that the N-terminal portion of HSP70 is the ATP-binding portion that is essential for protein refolding, and the C-terminus is the peptide binding, antiapoptotic portion of the molecule.

As such, the present provides surprisingly active and novel fusion proteins for the treatment of HSP70 related disorders or conditions. In particular, the present invention relates to novel compositions and methods of treating disease whereby a subject is administered a heat shock protein 70 conjugated or fused to an Fc fragment of an immunoglobulin. The present invention, including compounds, methods, and pharmaceutical compositions will be described with reference to the following definitions that, for convenience, are set forth below. Unless otherwise specified, the below terms used herein are defined as follows:

I. DEFINITIONS

As used herein, the term "a," "an," "the" and similar terms used in the context of the present invention (especially in the context of the claims) are to be construed to cover both the singular and plural unless otherwise indicated herein or clearly contradicted by the context.

As used herein, the term "HSP70" or "heat shock protein 70," which are used interchangeably herein, describes an exogenously derived heat shock protein characterized by its association with the art-recognized family of 70 kiloDalton heat shock proteins, the structures of which are well-known in that art. In addition, as used herein, the term "HSP70" covers native HSP70, recombinant HSP70, as well as derivatives thereof, e.g., PEG-HSP70. Moreover, the domain in a fusion protein that accounts for the HSP70 sequence/component of the fusion protein is described herein as the "HSP70 domain.

As used herein, "HSP70 related disorders or conditions" describes the class of conditions or disorders that are regulated by HSP70. Exemplary HSP70 related disorders or conditions include, but are not limited to myopathy, both congenital such as muscle dystrophies, and acquired such as rhabdomyolysis, polymyositis, and dermatomyositis; acute trauma; traumatic toxicosis due to crash injury; ischemia-reperfusion injury including stroke and myocardial infarction; heart failure; muscle damage as a result of the excessive physical exercise, e.g., without anabolic effects such as increase in body mass; cancer; fibrosis, including liver, pulmonary and cystic fibrosis; neurodegenerative diseases such as Alzheimer's, Huntington's, Parkinson's, and Amyotropic lateral sclerosis; certain inflammation; reduced physical performance (e.g., endurance), e.g., relative to absolute capability of individual; reduced mental performance, e.g., relative to absolute capability of individual; fatigue syndrome; sleep deprivation; sepsis; and hemorrhagic shock. In a particular example, the HSP70 related disorder or condition may be muscle degeneration and impairment stemming from various causes including tissue ischemia, severe injury, exercise-induced tissue injury and fatigue, advanced age, muscular dystrophy resulting form genetic defects and also caused by major diseases such as cancer, kidney failure and others. In a particular embodiment, the HSP70 related disorders or conditions is stroke or cancer, e.g., melanoma.

As used herein, the term "exogenous" describes the external origin of the HSP70, or alternatively stated, the exogenous HSP70 described herein, is derived or developed from outside the subject, e.g., through recombinant methods.

As used herein, the term "endurance" describes the ability to sustain a physical activity, perform repetitive submaximal contractions, or exert a force for a prolonged period. In certain embodiments, endurance may include aerobic endurance, anaerobic endurance, speed endurance, and strength endurance. In certain embodiments, increased endurance describes the ability to sustain the physical activity, contractions or force for a increased periods of time or with less exerted effort.

As used herein, the term "performance" describes the manner or quality of action taken, physically or mentally, to carry out a task. Increased mental or physical performance refers to the improved ability to carry out that task or multiple sequential tasks. Moreover, the compounds of the present invention are intended to affect improvement in physical performance or mental performance. In one embodiment the performance is physical performance. In certain embodiments where the performance is physical, the improved physical performance may include increased endurance, increased muscle power, or increased muscle strength. In another embodiment, the performance is mental performance. In certain embodiments where the performance is mental, the improved mental performance may include improved comprehension, improved memory retention, and improved mental acuity.

As used herein, and unless otherwise specified, the terms "treat," "treating" and "treatment" refer to the eradication or amelioration of a disease, disorder, or condition, or of one or more symptoms associated with the disease, disorder or condition. In certain embodiments, the terms refer to minimizing the advancement or worsening of the disease, disorder, or condition resulting from the administration of a compound of the invention to a patient with such a disease, disorder, or condition. In some embodiments, the terms refer to the administration of a compound provided herein, with or without other additional active agents, after the onset of symptoms of the particular disease, disorder, or condition. The terms "treating", "treatment", or the like, as used herein covers the treatment of a disease, disorder, or condition in a subject, e.g., a mammal, and includes at least one of: (i) inhibiting the disease, disorder, or condition, i.e., partially or completely halting its progression; (ii) relieving the disease, disorder, or condition, i.e. causing regression of symptoms of the disease, disorder, or condition, or ameliorating a symptom of the disease, disorder, or condition; and (iii) reversal or regression of the disease, disorder, or condition, preferably eliminating or curing of the disease, disorder, or condition. In a particular embodiment the terms "treating", "treatment", or the like, covers the treatment of a disease, disorder, or condition in a mammal, e.g., a primate, e.g., a human, and includes at least one of (i), (ii), and (iii) above. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, the terms "subject", and "patient" are used interchangeably. The terms "subject" and "patient" refer to an animal (e.g., a bird such as a chicken, quail or turkey) or a mammal including non-primates (e.g., a cow, pig, horse, sheep, rabbit, guinea pig, rat, cat, dog, and mouse) and primates (e.g., a monkey, chimpanzee and a human). In a particular embodiment, the subject is a human.

As used herein, and unless otherwise specified, the terms "prevent," "preventing" and "prevention" refer to the prevention of the onset, recurrence or spread of a disease, disorder, or condition, or of one or more symptoms thereof. In certain embodiments, the terms refer to the administration of an HSP70 fusion protein to a subject, with or without other additional active compounds, prior to the onset of symptoms, particularly to patients at risk of a disease, disorder, or condition provided herein. The terms encompass the inhibition or reduction of a symptom of the particular disease, disorder, or condition. Subjects with familial history of a disease, disorder, or condition, in particular, are candidates for preventive regimens in certain embodiments. In addition, subjects who have a history of recurring symptoms are also potential candidates for the prevention. In this regard, the term "prevention" may be interchangeably used with the term "prophylactic treatment." In certain embodiments, the prevention is achieved by administration of a prophylactically effective amount of a degradation resistant formulation of the invention.

As used herein, and unless otherwise specified, a "therapeutically effective amount" of an active agent, e.g., an HSP70 fusion protein, is an amount sufficient to provide a therapeutic benefit in the treatment or management of a disease, disorder, or condition, or to delay or minimize one or more symptoms associated with the disease, disorder, or condition. A therapeutically effective amount of an HSP70 fusion protein means an amount of an HSP70 fusion protein, alone or in combination with other therapies, which provides a therapeutic benefit in the treatment or management of the disease, disorder, or condition. The term "therapeutically effective amount" can encompass an amount that improves overall therapy, reduces or avoids symptoms or causes of disease, disorder, or condition, or enhances the therapeutic efficacy of another therapeutic agent.

As used herein, and unless otherwise specified, the terms "manage," "managing" and "management" refer to preventing or slowing the progression, spread or worsening of a disease, disorder, or condition, or of one or more symptoms thereof. Often, the beneficial effects that a subject derives from a prophylactic and/or therapeutic agent do not result in a cure of the disease, disorder, or condition. In this regard, the term "managing" encompasses treating a subject who had suffered from the particular disease, disorder, or condition in an attempt to prevent or minimize the recurrence of the disease, disorder, or condition.

As used herein, and unless otherwise specified, a "prophylactically effective amount" of an active agent, e.g., an HSP70 fusion protein, is an amount sufficient to prevent a disease, disorder, or condition, or prevent its recurrence. A prophylactically effective amount of an HSP70 fusion protein means an amount of an HSP70 fusion protein, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "polyethylene glycol" or "PEG" refers to a polyalkylene glycol compound or derivative thereof, with or without coupling agents or derivatization with coupling or activating moieties. In its typical form, PEG is a linear polymer with terminal hydroxyl groups and has the formula HO—$CH_2CH_2$—$(CH_2CH_2O)_n$—$CH_2CH_2$—OH. The number of repeating subunits "n" in the PEG is approximated for the molecular mass described in Daltons.

The term "Fc region" or "Fc domain" is art-recognized, and describes the C-terminal region of an immunoglobulin heavy chain, including native sequence Fc regions and variant Fc regions. In certain embodiments, although the boundaries of the Fc region of an immunoglobulin heavy chain might vary, the human IgG heavy chain Fc region is usually defined to stretch from an amino acid residue at position Cys226, or from Pro230, to the carboxyl-terminus of the immunoglobulin. The C-terminal lysine (residue 447 according to the EU numbering system) of the Fc region may be removed, for example, when recombinantly engineering the nucleic acid encoding a heavy chain of the antibody. Unless indicated otherwise, herein the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

A "native sequence Fc region" comprises an amino acid sequence identical to the amino acid sequence of a Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region, as well as naturally occurring variants thereof.

A "variant Fc region" comprises an amino acid sequence, which differs from that of a native sequence Fc region by virtue of at least one amino acid modification, preferably one or more amino acid substitution(s). In certain embodiments, the variant Fc region has at least one amino acid substitution compared to a native sequence Fc region or to the Fc region of a parent polypeptide, e.g. from about one to about ten amino acid substitutions, e.g., from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

II. HSP70 FUSION PROTEINS OF THE INVENTION

The novel compounds of the invention, HSP70 fusion proteins, or derivatives thereof, may be used in the formulations and the methods of treatment of the invention. In one embodiment, the invention is an HSP70 fusion protein comprising (i) a first HSP70 domain fused to (ii) a second Fc domain, wherein the first and second domains are optionally linked by a third linker domain. In certain embodiments, the HSP70 domain is human heat shock protein 70, e.g., a recombinant human heat shock protein 70 (rhHSP70). In certain embodiments, the HSP70 in its native form, or a derivatized form, e.g., pegylated (PEG-HSP70), conjugated or fused with an Fc fragment of immunoglobulin, e.g., immunoglobulin G (IgG).

In certain embodiments of the invention, the Fc domain is a constant Fc fragment of human immunoglobulin G (IgG). The Fc fragment of immunoglobulins, such as immunoglobulin G (IgG), are known to have long half-lives due to their propensity for being recycled in the vascular endothelium. Specifically, when IgG enters the endosomes of these epithelial cells, the neonatal Fc receptor FcRn binds to the Fc fragment of IgG. This binding of FcRn to Fc has been experimentally found to enhance the recycling of IgG back to the cell surface, which decreases the amount of IgG that is degraded in the lysosomes. In particular embodiments, the IgG may be selected from IgG1, IgG2, IgG3, or IgG4, e.g., IgG1 or IgG3.

In certain embodiments of the invention, the linker domain is present, and comprises a spacer moiety. In particular embodiments, where the linker domain is present, the linker domain may also comprise a cleavable moiety, e.g., cleavable by the action of a protease, e.g., a TEV protease. In certain alternate embodiments of the invention, the linker domain is absent.

In certain embodiments of the invention, the Fc domain is fused to the C-terminus of the HSP70 domain. As noted herein above, the C-terminus is known to be integrally involved in binding, i.e., the peptide binding, antiapoptotic portion of the molecule.

In certain embodiments of the invention, the Fc domain is fused to the N-terminus of the HSP70 domain. As noted herein above, the N-terminus is known to be integrally involved in refolding.

In certain embodiment of the invention, the HSP70 conjugated or fused within the Fc fragment of immunoglobulin, e.g., IgG, is recombinant HSP70, e.g., recombinant human HSP70 (rhHSP70). In certain embodiment of the invention, the HSP70 conjugated or fused within the Fc fragment of immunoglobulin, e.g., IgG, is a derivatized recombinant HSP70, e.g., pegylated recombinant human HSP70 (PEG-rhHSP70). Moreover, the native HSP70 amino acid sequence is set forth in GeneBank, Accession No. AAD21816 and expressed by cDNA set forth in Genebank, Accession No. M24743, Hunt et al., 1985, Proc. Natl. Acad. Sci. 82:6455-6489. To produce rhHSP70, hHSP70 cDNA may be cloned, for example, into the pET27a vector (Novagen) to form expression vector pET27hhsp70 that may then be transfected into K12 *Escherichia coli* strain HMS174(DE3) (Novagen).

In certain embodiments of the invention, the HSP70 fusion protein is an amino acid sequence represented by SEQ ID NO: 1 (the amino acid sequence of the HSP70-Fc fusion protein is shown below).

```
              10         20         30         40         50         60
       THTCPPCPAP ELLGGPSVFL FPPKPKDTLM ISRTPEVTCV VVDVSHEDPE VKFNWYVDGV 70         80         90        100        110        120
       EVHNAKTKPR EEQYNSTYRV VSVLTVLHQD WLNGKEYKCK VSNKALPAPI EKTISKAKGQ 130        140        150        160        170        180
       PREPQVYTLP PSRDELTKNQ VSLTCLVKGF YPSDIAVEWE SNGQPENNYK TTPPVLDSGD 190        200        210        220        230        240
       SFFLYSKLTV DKSRWQQGNV FSCSVMHEAL HNHYTQKSLS LSPGKASGAG STTENLYFQG 250        260        270        280        290        300
       GSMAKAAAIG IDLGTTYSCV GVFQHGKVEI IANDQGNRTT PSYVAFTDTE RLIGDAAKNQ 310        320        330        340        350        360
       VALNPQNTVF DAKPLIGRKF GDPVVQSDMK HWPFQVINDG DKPKVQVSYK GDTKAFYPEE 370        380        390        400        410        420
       ISSMVLTKMK EIAEAYLGYP VTNAVITVPA YFNDSQRQAT KDAGVIAGLN VLRIINEPTA 430        440        450        460        470        480
       AAIAYGLDRT GKGERNVLIF DLGGGIFDVS ILTIDDGIFE VKATAGDTHL GGEDFDNRLV
```

-continued

```
        490        500        510        520        530        540
NHFVEEFKRK HKKDISQNKR AVRRLRTACE RAKRTLSSST QASLEIDSLF EGIDFYTSIT 550        560        570        580        590        600
RARFEELCSD LFRSTLEPVE KALRDAKLDK AQIHDLVLVG GSTRIPKVQK LLQDFFNGRD 610        620        630        640        650        660
LNKSINPDEA VAYGAAVQAA ILMGDKSENV QDLLLLDVAP LSLGLETAGG VMTALIKPNS 670        680        690        700        710        720
TIPTKQTQIF TTYSDNQPGV LIQVYEGERA MTKDNNLLGR FELSGIPPAP RGVPQIEVTF 730        740        750        760        770        780
DIDANGLINV TATDKSTGKA NKITITNDKG RLSKEEIERM VQEAEKYKAE DEVQRERVSA 790        800        810        820        830        840
KNALESYAFN MKSAVEDEGL KGKISEADKK KVLDKCQEVI SWLDANTLAE KDEFEHKRKE 850        860        870        880
LEQVCNPIIS GLYQGAGGPG PGGFGAQGPK GGSGSGPIIE EVD

MW: 99.4 kDa. SEQ ID NO: 1
AA1-225 Fc fragment
AA226-233 Linker region (spacer moiety)
AA234-242 proteolytic TEV sequence (cleavable moiety)
AA243-883 human HSP70 (linked at N-terminus)
```

In particular embodiments, the HSP70 fusion proteins of the invention, e.g., the rhHSP70-Fc fusion, e.g., SEQ ID NO: 1, show a rate of clearance from serum that is at least an order of magnitude slower than the rhHSP70.

In particular embodiments, the HSP70 fusion proteins of the invention, e.g., the rhHSP70-Fc fusion, e.g., SEQ ID NO: 1, have a bioavailability at least an order of magnitude higher in intrapulmonary and nasal administration than rhHSP70.

In certain embodiments, the HSP70 fusion proteins of the invention, e.g., the rhHSP70-Fc fusion, e.g., SEQ ID NO: 1, show high efficacy in treating malignant tumors.

In particular embodiments, the Fc fusion protein described herein has a heterologous portion fused to the N-terminus of the C-terminal portion of an immunoglobulin Fc domain. Preferably, a sequence beginning in the hinge region just upstream of the papain cleavage site, e.g., taking the first residue of heavy chain constant region to be 114 or analogous sites of other immunoglobulins, is used in the fusion. In one embodiment, the heterologous domain is fused to the hinge region and CH2 and CH3 or CH1, hinge, CH2 and CH3 domains of an IgG1, IgG2, or IgG3 heavy chain. In certain embodiments, the precise site at which the fusion is made is not critical, and the optimal site may be determined by routine experimentation.

For human Fc domains, in certain embodiments, the use of human IgG1 and IgG3 immunoglobulin sequences is selected. An advantage of using IgG1 is that an IgG1 fusion protein may be more easily purified efficiently on immobilized protein A. Alternatively, purification of IgG3 fusion proteins requires protein G, a significantly less versatile medium. However, other structural and functional properties of immunoglobulins should be considered when choosing the IgG fusion partner for a particular construction. For example, the IgG3 hinge is longer and more flexible, so it can accommodate a larger heterologous portion that may not fold or function properly when fused to IgG1. Another consideration may be valence: IgG immunoadhesins are bivalent homodimers, whereas Ig subtypes like IgA and IgM may give rise to dimeric or pentameric structures, of the basic Ig homodimer unit, respectively.

For Fc fusion proteins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life in approximately one third of the other IgG isotypes. However, the selection the particular immunoglobulin will be dependent upon the combination of these factors and the intended function.

Another important consideration for Fc fusion proteins designed to be used as human therapeutics is the number of allotypic variants of the particular isotype. In general, IgG isotypes with fewer serologically-defined allotypes are preferred. For example, IgG1 has only four serologically-defined allotypic sites, two of which are located in the Fc region; and one of these sites is non-immunogenic. Alternatively, there are 12 serologically-defined allotypes in IgG3, all of which are in the Fc region; only three of these sites have one allotype which is non-immunogenic. Thus, the potential immunogenicity of an IgG3 fusion protein is greater than that of an IgG1 fusion protein.

In certain embodiments, an Fc domain used in the HSP70 fusion proteins may comprise one or more alterations as compared to the wild-type Fc domain. These Fc domains would nonetheless retain substantially the same characteristics required for therapeutic utility as compared to their wild-type counterpart. For example, it is thought that certain alterations can be made in the Fc region that would result in altered (i.e., either improved or diminished) Ciq binding and/or Complement—Dependent Cytotoxicity (CDC), e.g., as described in WO99/51642. See also Duncan et al., Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein that improve binding of the Fc region to FcRn. Polypeptide variants with altered Fc region amino acid sequences and increased or decreased C1q binding capability are described in U.S. Pat. No. 6,194,551; WO99/51642; Idusogie et al. J. Immunol. 164: 4178-4184 (2000). The contents of these are specifically incorporated herein by reference. An exemplary Fc domain is shown below:

(SEQ ID NO: 2)
THTCPPCPAPELLGGPSVFLFPPKPKDTLMISRTPEVTCVVVDVSHE

DPEVKFNWYVDGVEVHNAKTKPREEQYNSTYRVVSVLTVLHQDWLNG

KEYKCKVSNKALPVPIEKTISKAKGQPREPQVYTLPPSREEMTKNQV

SLTCLVKGFYPSDIAVEWESNGQPENNYKTTPPVLDSDGPFFLYSKL

TVDKSRWQQGNVFSCSVMHEALHNHYTQKSLSLSPGK

An example of an advantageous linker (TG3) and Fc domain combined is shown below:

(SEQ ID NO: 3)
TGGGTHTCPPCPAPELLGGPSVFLFPPKPKDTLMISRTPEVTCVVVD

VSHEDPEVKFNWYVDGVEVHNAKTKPREEOYNSTYRVVSVLTVLHOD

WLNGKEYKCKVSNKALPAPIEKTISKAKGOPREPOVYTLPPSREEMT

KNOVSLTCLVKGFYPSDIAVEWESNGOPENNYKTTPPVLDSDGSFFL

YSKLTVDKSRWQQGNVFSCSVMHEALHNHYTQKSLSLSPGK

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcy receptor relative to a wild-type Fc domain. In other cases, the mutant Fc domain having one or more of these mutations (e.g., Asn-434 mutation) has increased ability of binding to the MHC class I-related Fc-receptor (FcRN) relative to a wild-type Fc domain.

A. Radiolabeled HSP70 In a murine colon carcinoma model, it was shown that intratumoral co-injection of HSP70 and dendritic cells (DC) into the irradiated tumor site induce a more potent antitumor response than injection of the DC alone (Y.-S. Wang, S.-C. Liu, C-C. Chang, Y.-C. Huang, W.-L. Fong, M-S. Chi, K.-H. Chi., Recombinant heat shock protein 70 in combination with radiotherapy as a source of tumor antigens to improve dendritic cell immunotherapy, Front. Oncol. 2012 (2)148). HSP70 was effective in inducing a tumor-specific cytotoxic T lymphocyte response or tumor growth delay. These results demonstrate that co-administration of HSP70 and radiation therapy could be a new way of cancer radioimmunotherapy. Combination of these two modalities, immunotherapy and radiotherapy, in the same compound may be used, as described herein, as an effective strategy of cancer treatment.

Moroever, $^{131}$I-labeled IL-8, a cytokine that mediate neutrophil activation, has been shown to aid imaging infection in human (M. D. Gross, B. Shapiro, L. M. Fig, R. Steventon, R. W. S Skinner, R. V. Hay, Imaging of Human Infection with $^{131}$I-labeled Recombinant Human Interleukin-8, J. Nucl. Med., 2001 (42(11))1656). While I-125 brachytherapy is used clinically for prostate cancer, in a different study, an anti-intercellular adhesion molecule 1 (ICAM-1) antibody, a pro-inflammatory cytokine, has been conjugated to the $^{125}$I-labeled gold nanoparticles and used for imaging of the arthritic rats by gamma camera. (X. Shao, H. Zhang, J. Rajian, D. L. Chamberland, P. Sherman, C. A. Quesada, A. Koch., N. Kotov, X. Wang, $^{125}$I-labeled Gold Nanorods for Targeted Imaging of inflammation, ACS Nano, 2011 (5911)) 8967). Such studies lend weight to the notion that a radioactive isotope may coincidentally serve both a treatment and an imaging function.

As such, in one embodiment of the invention, the HSP70 fusion protein may be labeled with one or more radioactive isotopes, e.g., selected from the group consisting of I-123, I-124, I-125 and I-131. These radioactive isotopes, in certain embodiments, deliver gamma radiation to cancer cells, and may serve as the source of energy suitable for use in imaging the cancer as well.

III. METHODS OF THE INVENTION

The invention relates to the method of use of a compound or formulations of the invention, which contain a heat shock protein 70, e.g., a recombinant human heat shock protein 70, for the treatment of HSP70 related disorders or conditions. For example, in one embodiment, the invention provides a method of treatment of an HSP70 related disorder or condition, wherein the method comprises administering to a subject, e.g., a mammal, a therapeutically effective amount of an HSP70 fusion protein of the invention (e.g., wherein the HSP70 fusion protein comprises (i) a first HSP70 domain fused to (ii) a second Fc domain, wherein the first and second domains are optionally linked by a third linker domain), such that the HSP70 related disorder or condition is treated in the subject.

In certain embodiments of the invention, the HSP70 related disorder or condition is selected from the group consisting of myopathy, both congenital such as muscle dystrophies, and acquired such as rhabdomyolysis, polymyositis, and dermatomyositis; acute trauma; traumatic toxicosis due to crash injury; ischemia-reperfusion injury including stroke and myocardial infarction; heart failure; muscle damage as a result of the excessive physical exercise, e.g., without anabolic effects such as increase in body mass; cancer; fibrosis, including liver, pulmonary and cystic fibrosis, neurodegenerative diseases such as Alzheimer's, Huntington's, Parkinson's, and Amyotropic lateral sclerosis; certain inflammation; reduced physical performance (e.g., endurance), e.g., relative to absolute capability of individual; reduced mental performance, e.g., relative to absolute capability of individual; fatigue syndrome; sleep deprivation; sepsis; and hemorrhagic shock. In a particular example, the HSP70 related disorder or condition may be muscle degeneration and impairment stemming from various causes including tissue ischemia, severe injury, exercise-induced tissue injury and fatigue, advanced age, muscular dystrophy resulting form genetic defects and also caused by major diseases such as cancer, kidney failure and others.

In particular embodiments of the invention, the HSP70 related disorder or condition is selected from the group consisting of cancer; sepsis; cardiac injury; muscular injury and degeneration; fibrosis, including liver, pulmonary and cystic fibrosis; recovery from physical and exercise stress; neurodegeneration including Parkinson disease, Alzheimer disease, Huntington disease, and amyotrophic lateral sclerosis; spinal cord injury; traumatic brain injury; stroke; acute lung injury; eye neurodegenerative diseases including glaucoma and macular degeneration; and epilepsy.

In a specific embodiment, the HSP70 related disorder is sarcopenia, e.g., as associated with aging and the progressive decline of muscle mass, strength, and quality. In another specific embodiment, the HSP70 related condition is reduced physical performance (e.g., endurance), or reduced mental performance, wherein the performance (or endurance) is increased by treatment with the compounds of the invention. In another specific embodiment, the HSP70 related disorder is fatigue syndrome. In another specific embodiment, the HSP70 related disorder or condition is muscle damage or muscle degeneration. In another specific embodiment, the HSP70 related disorder or condition is cancer, e.g., melanoma. In another specific embodiment, the HSP70 related disorder or condition is stroke.

In another embodiment, the invention provides a method to increase performance, alleviate fatigue syndrome, or treat muscle damage or muscle degeneration comprising administering to a mammal, e.g., a human, a therapeutically effective amount of HSP70 fusion protein, and wherein the HSP70 fusion protein comprises (i) a first HSP70 domain fused to (ii) a second Fc domain, wherein the first and second domains are optionally linked by a third linker domain, such that performance is increased, the fatigue syndrome is alleviated, or the muscle damage or muscle degeneration is treated in the mammal.

In another embodiment, the invention provides a method of radioimmunotherapy comprising administering to a subject a therapeutically effective amount of HSP70 fusion protein, wherein the HSP70 fusion protein comprises (i) a first HSP70 domain fused to (ii) a second Fc domain, wherein the first and second domains are optionally linked by a third linker domain, and wherein the HSP70 fusion protein is labeled with one or more radioactive isotopes, such that cancer, e.g., melanoma, is treated in the subject. In certain embodiments, the radioactive isotope is selected from the group consisting of I-123, I-124, I-125 and I-131. The method may further comprise the step of using the radioactive isotopes to image the cancer.

In certain embodiments of the methods of invention, the HSP70 fusion protein is an amino acid sequence represented by SEQ ID NO: 1.

In certain embodiments of the invention, the HSP70 is recombinant human HSP70.

In certain embodiments of the invention, the HSP70 is pegylated HSP70.

In certain embodiments of the invention, the subject is mammal.

In certain embodiments of the invention, the mammal is human.

In certain embodiments of the invention, the formulation is administered intravenously, intrapulmonarily, subcutaneously, intranasally, orally, or by inhalation.

In addition, the present invention is intended to include any novel method of preparation of the compounds or formulations of the present invention.

In certain embodiments, the HSP70 fusion protein shows a rate of clearance from serum that is at least an order of magnitude slower than the HSP70 alone.

In certain embodiments, the formulation is administered intrapulmonarily or intranasally. In particular embodiments of these intrapulmonarily or intranasally administered HSP70 fusion proteins, the HSP70 fusion proteins may show a bioavailability that is at least an order of magnitude higher than the HSP70 alone.

Without wishing to be bound by theory, in certain embodiments it is believed that HSP70 fusion proteins of the present invention may confer its action by stimulating proangiogenesis and activating satellite cells—a key population of the muscle stem cells.

IV. FORMULATIONS OF THE INVENTION

The formulations of the invention comprise HSP70 fusion proteins of the invention, e.g., a therapeutically effective amount of an HSP70 fusion protein, and may utilize any administration route that does not significantly impair the ability of the HSP70 fusion protein to perform its intended function, e.g., intravenous injections, oral administration, nasal administration, intrapulmonary administration, intravaginal administration, rectal administration, or administration through inhalation.

As such, one embodiment of the invention provides a pharmaceutical composition comprising an HSP70 fusion protein of the invention, e.g., a therapeutically effective amount of an HSP70 fusion protein of the invention, and pharmaceutically acceptable carrier. In certain embodiments of the invention, the formulation comprising a compound of the invention is formulated for intravenous, intrapulmonary, subcutaneous, intranasal, oral, or inhalation administration. For example, the HSP70 fusion protein may comprise (i) a first HSP70 domain fused to (ii) a second Fc domain, wherein the first and second domains are optionally linked by a third linker domain, and pharmaceutically acceptable carrier. In certain embodiments, the HSP70 fusion protein is an amino acid sequence represented by SEQ ID NO: 1.

In certain embodiments of the invention, the HSP70 fusion protein is labeled with one or more radioactive isotopes, e.g., selected from the group consisting of I-123, I-124, I-125 and I-131.

In certain embodiments of the invention, the HSP70 is recombinant human HSP70.

In certain embodiments of the invention, the HSP70 is pegylated HSP70, e.g., pegylated recombinant human HSP70, e.g., PEG-rhHSP70.

An HSP70 fusion protein of the invention, e.g., rhHSP70-Fc, can be formulated in a pharmaceutical composition comprising a therapeutically effective amount of the HSP70 and a pharmaceutical carrier. A "therapeutically effective amount" is an amount sufficient to provide the desired therapeutic result. Preferably, such amount has minimal negative side effects. The amount of rhHSP70-Fc administered to treat a condition treatable with rhHSP70 is based on HSP70 activity of the conjugated protein, which can be determined by HSP70 activity assays known in the art. The therapeutically effective amount for a particular patient in need of such treatment can be determined by considering various factors, such as the condition treated, the overall health of the patient, method of administration, the severity of side-effects, and the like.

In certain embodiments, to prepare pharmaceutical compositions containing an HSP70 fusion protein of the invention, e.g., rhHSP70-Fc, a therapeutically effective amount of the material is admixed with a pharmaceutically acceptable carrier or excipient. Preferably the carrier or excipient is inert. A pharmaceutical carrier can be any compatible, non-toxic substance suitable for delivering the HSP70 compositions of the invention to a patient. Examples of suitable carriers include normal saline, Ringer's solution, dextrose solution, and Hank's solution. Non-aqueous carriers such as fixed oils and ethyl oleate may also be used. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives.

Compositions of the invention can be administered orally or injected into the body. Injections are usually intramuscular, subcutaneous, intradermal or intravenous. Alternatively, intra-articular injection or other routes could be used in appropriate circumstances. When administered parenterally, HSP70-Fc is preferably formulated in a unit dosage injectable form (solution, suspension, emulsion) in association with a pharmaceutical carrier. See, e.g., Avis et al., eds., *Pharmaceutical Dosage Forms: Parenteral Medications*, Dekker, N.Y. (1993); Lieberman et al., eds., *Pharmaceutical Dosage Forms: Tablets*, Dekker, N.Y. (1990); and Lieberman et al., eds., *Pharmaceutical Dosage Forms: Disperse Systems*, Dekker, N.Y. (1990). Alternatively, compositions of the invention may be introduced into a patient's body by implantable or injectable drug delivery system, e.g., Urquhart et al. *Ann. Rev. Pharmacol. Toxicol* 24:199-236, (1984); Lewis, ed., *Controlled Release of Pesticides and Pharmaceuticals*, Plenum Press, New York (1981); U.S. Pat. Nos. 3,773,919; 3,270,960; and the like. The HSP70 fusion protein can be administered in aqueous vehicles such as water, saline or buffered vehicles with or without various additives and/or diluting agents. Preparation of such pharmaceutical compositions is known in the art; see, e.g., *Remington's Pharmaceutical Sciences and U.S. Pharmacopeia: National Formulary*, Mack Publishing Company, Easton, Pa. (1984).

A. Administration of Formulations of the Present Invention

In general, however, the formulations of the invention that comprise HSP70 fusion proteins can be administered in a variety of dosage forms that do not affect or significantly detract from the increased stability of the HSP70 fusion proteins (i.e., allowing such formulations to achieve their desired function) including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form. The oral dosage form can be a tablet or a caplet. The formulations can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the formulations comprising the HSP70 fusion proteins are delivered to a desired site, such as the brain, by continuous injection via a shunt. In another embodiment, the formulations comprising the HSP70 fusion proteins are delivered to a desired malignant tumor site, such as melanoma, by intratumoral injection.

In another embodiment, the formulations of the invention can be administered parenterally, such as intravenous (i.v.) administration. The formulations for administration will commonly comprise a solution of HSP70 fusion protein dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of HSP70 fusion protein in these formulations can vary widely, and will be selected primarily based on fluid volumes, viscosities, body weight, and the like, in accordance with the particular mode of administration selected and the patient's needs. For i.v. administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, HSP70 fusion proteins can be administered by introduction into the central nervous system of the subject, e.g., into the cerebrospinal fluid of the subject. The formulations for administration will commonly comprise a solution of HSP70 fusion protein dissolved in a pharmaceutically acceptable carrier. In certain aspects, HSP70 is introduced intrathecally, e.g., into a cerebral ventricle, the lumbar area, or the cisterna magna. In another aspect, HSP70 fusion protein is introduced intraocullarly, to thereby contact retinal ganglion cells.

The pharmaceutically acceptable formulations can be suspended in aqueous vehicles and introduced through conventional hypodermic needles or using infusion pumps. Prior to introduction, the formulations can be sterilized with, preferably, gamma radiation or electron beam sterilization.

For oral administration, the compounds will generally be provided in unit dosage forms of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include, but are not limited to sodium and calcium carbonate, sodium and calcium phosphate, and lactose, while corn starch and alginic acid are suitable disintegrating agents. Binding agents may include, but are not limited to starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of HSP70 fusion protein with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethylcellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active HSP70 fusion protein doses.

For transmucosal administration (e.g., buccal, rectal, nasal, ocular, etc.), penetrants appropriate to the barrier to be permeated are used in the formulation. Such penetrants are generally known in the art.

In particular, formulations of the invention may be administered to the nasal cavity in any suitable form. For example, the formulations of the invention may be administered to the nasal cavity in the form of drops or a spray, or the powders of the invention may be administered in aerosolized form. One method of administering the formulations of the invention would be to use a spray device. Spray devices can be single ("unit") dose or multiple dose systems, for example comprising a bottle, pump and actuator, and are available from various commercial sources, including Pfeiffer (Germany), Valois (France), Calmar (Germany), Ursatech (Germany), Bespak (UK) and Becton-Dickinson (USA). Electrostatic spray devices, such as described in U.S. Pat. No. 5,655,517, are also suitable for the intranasal administration of the formulations of the invention.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the HSP70 will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The suppositories for rectal administration of HSP70 fusion proteins can be prepared by mixing the drug with a suitable non-irritating excipient, which is solid at ordinary temperatures but liquid at the rectal temperatures and will therefore melt in the rectum to release the drug. Such materials are cocoa butter and polyethylene glycols.

The compounds can be delivered transdermally, by a topical route, formulated as applicator sticks, solutions, suspensions, emulsions, gels, creams, ointments, pastes, jellies, paints, powders, or aerosols.

The HSP70 fusion proteins may also be presented as aqueous or liposome formulations. Aqueous suspensions can contain HSP70 fusion protein in admixture with excipients suitable for the manufacture of aqueous suspensions. Such excipients include, but are not limited to a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending HSP70 fusion proteins in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the HSP70 fusion proteins may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In general a suitable dose will be in the range of 0.001 to 10 mg per kilogram body weight of the recipient per day, preferably in the range of 0.005 to 1 mg per kilogram body weight per day. The desired dose is preferably presented once daily, but may be dosed as two, three, four, five, six or more subdoses administered at appropriate intervals throughout the day.

The HSP70 fusion proteins can be administered as the sole active agent, or in combination with other known therapeutics to be beneficial in the treatment of related HSP70 disorders or conditions. In any event, the administering physician can provide a method of treatment that is prophylactic or therapeutic by adjusting the amount and timing of drug administration on the basis of observations of one or more symptoms of the disorder or condition being treated.

Details on techniques for formulation and administration are well described in the scientific and patent literature, see, e.g., the latest edition of Remington's Pharmaceutical Sciences, Maack Publishing Co, Easton Pa. ("Remington's"). After a pharmaceutical composition has been formulated in an acceptable carrier, it can be placed in an appropriate container and labeled for treatment of an indicated condition). For administration of the HSP70, such labeling would include, e.g., instructions concerning the amount, frequency and method of administration.

EXEMPLIFICATION

The present invention is illustrated by the following examples, which are not intended to be limiting in any way.

A. Establishment of Activity Profiles of HSP70 and HSP70-PEG i. Synthetic Preparations of HSP70 and -HSP-70-PEG Example 1

Fermentation of rhHSP70

To prepare sufficient amounts of HSP70, 5 L of the *E. coli* expression strain HMS174 (DE3) hHSP70 may be grown in animal free medium containing 12 g phytone peptone, 60 g yeast extract, 40 g sodium chloride, 1 g methionine, and water to 5 liters. Before inoculation with expression strain bacteria, the medium may be sterilized, and supplemented with kanamycin to a final concentration of 30 mcg per milliliter. The medium may then be inoculated with one liter of an overnight culture of the HMS174(DE3) bacteria. The pH, level of dissolved oxygen and temperature inside the fermenter reactor may be carefully monitored. When the culture reaches an optical density of approximately 1.2 (for example, approximately 2.5 hours after inoculation), IPTG (isopropyl-B-D-thiogalactopyranoside) may be added to a final concentration of 1 mM to initiate the induction of expression of rhHSP70. Growth may then be continued until an optical density of approximately 2.7 is attained (for example, after an additional 3.5 hours following addition of IPTG). The fermented bacteria may then be harvested by centrifugation using standard techniques. The bacterial pellet may be re-suspended in 1 L of the 10 mmol PBS buffer (1 mmol EDTA, 10% glycerol). The re-suspended bacteria may then optionally be frozen on dry ice before further processing. To continue processing, the frozen bacteria may be thawed if necessary, and then may be disrupted by pressure lysis. The resulting lysate may then be cleared and sterile filtered.

Example 2

Purification of rhHSP70

A bacterial lysate comprising rhHSP70 may be subjected to the following two-step purification protocol. The specific example provided utilizes 500 mL of lysate; adjustments may be made for different lysate volumes. In the first step of the protocol, 500 mL of the cleared lysate, prepared as set forth above, may be diluted two-fold with 10 mM sodium phosphate buffer pH 7.0. This 1 L of diluted and cleared bacterial lysate may be loaded onto a of DEAE Sephacel (Pharmacia) column (13 cm×15 cm) previously equilibrated with 2 column volumes of buffer A (10 mM sodium phosphate buffer pH 7.0, 20 mM sodium chloride, 10 mM ammonium sulfate). The elution is carried out with two column volumes of buffer B (20 mM sodium phosphate buffer pH 7, 85 mM sodium chloride, 10 mM ammonium sulfate). About 2 L of eluate is expected for recovery. The eluate may then be diafiltered (buffer exchanged) against a 10-fold volume of buffer C (20 mM sodium citrate pH 6.0, 100 mM sodium chloride, 10 mM ammonium sulfate).

In the second step of the protocol, a 700 mL column (13 cm×5.5 cm) ATP agarose (Sigma-Aldrich) may be equilibrated in one column volume of buffer D (20 mM sodium citrate pH 6.0, 85 mM sodium chloride, 10 mM ammonium sulfate). And the diafiltered solution may be run over the ATP agarose column. The column may then be washed with six column volumes of buffer D and finally eluted with 2 column volumes of buffer E (20 mM sodium citrate pH 6.0, 100 mM sodium chloride, 10 mM ammonium sulfate, 1 mM magnesium acetate, 1 mM ATP). The eluted material, human rhHSP70 having a purity of greater than 95 percent may be buffer exchanged into phosphate buffered saline and concentrated to a final concentration of 10-20 mg/ml, and then sterile filtered.

Example 3

PEGylation Techniques

The efficacy of a therapeutic agent may be enhanced by improving its bioavailability via several means, one of which is PEGylation, a process of chemically linking polyethylene glycol (PEG) to the therapeutic agent of interest, with the resulting conjugate exhibiting an increased serum half-life. Additional advantages of the PEGylated products may also include lower immunogenicity, decreased dosing frequency, increased solubility, enhanced stability, and reduced renal clearance. Because the most common reactive sites on proteins (including peptides) for attaching PEG are the $\epsilon$ amino groups of lysine and the a amino group of the N-terminal residue, early methods of PEGylation resulted in modification of multiple sites, yielding not only monoPEGylated conjugates consisting of mixtures of positional isomers, such as PEGINTRON™ (Grace et al., J. Biol. Chem. 2005; 280: 6327) and PEGASYS® (Dhalluin et al., Bioconjugate Chem. 2005; 16:504), but also adducts comprising more than one PEG chain.

The PEG reagents that are used to prepare PEGylated compounds of the invention may comprise a heterogenous mixture of PEGs having a different number (n) of ethylene glycol subunits in the PEG polymer. A single ethylene glycol subunit ($-(CH_2CH_2O)$) of PEG has a molecular weight of about 44 Daltons. Therefore, the molecular weight of the PEG polymer depends on the number (n). The PEGs attached to the PEGylated rhHSP70 compounds of the present invention will have n in the range from about 400 to about 1000 subunits. Preferably, the PEGs attached to the PEGylated HSP70 compounds of the present invention will have n in the range from about 400 to about 750.

A. Activated PEG for Amino or Imino Conjugation

To conjugate PEG to HSP70, an activated linker covalently attached to one or more PEG molecules may be reacted with an amino or imino group of an amino acid residue, e.g., with an alpha amino group at the N-terminus of HSP70, to form a PEG-HSP70 of the present invention.

A linker is "activated" if it is chemically reactive and ready for covalent attachment, e.g., to an amino group on an amino acid residue. Any activated linker can be used in this invention provided it can accommodate one or more PEG molecules and form a covalent bond, e.g., with an amino group of an amino acid residue under suitable reaction conditions. For example, the activated linker attaches to an alpha amino group in a highly selective manner over other attachment sites, e.g., epsilon amino group of lysine or imino group of histidine.

Activated PEG can be represented by the formula: $(PEG)_b$-L', where PEG covalently attaches to a carbon atom of the linker to form an ether bond, b is 1 to 9 (i.e. 1 to 9 PEG molecules can be attached to the linker), and L' contains a reactive group (an activated moiety) that can react with an amino or imino group on an amino acid residue to provide a covalent attachment of the PEG to HSP70.

In one embodiment, an activated linker (L') of the invention contains an aldehyde of the formula RCHO, where R is a linear (straight chain) or branched $C_{1-11}$ alkyl. After covalent attachment of an activated linker to HSP70, the linker (referred to as "-L-" in the structural formulas recited herein) between the HSP70 and PEG contains 2 to 12 carbon atoms. Propionaldehyde is an example of an activated linker of this invention. PEG-propionaldehyde, and is described in U.S. Pat. No. 5,252,714 and is commercially available from Shearwater Polymers (Huntsville, Ala.); represented by the formula PEG-$CH_2CH_2CHO$.

In certain embodiments, a suitable activated branched (also known as "multi-armed") linker can be used. Any suitable branched PEG linker that covalently attaches two or more PEG molecules to an amino group on an amino acid residue of HSP70, e.g., to an alpha amino group at the N-terminus, can be used. A branched linker used in this invention may contain two or three PEG molecules. For example, a branched PEG linker used in this invention can be a linear or branched aliphatic group that is hydrolytically stable and contains an activated moiety, e.g., an aldehyde group, which reacts with an amino group of an amino acid residue, as described above. The aliphatic group of a branched linker may contain 2 to 12 carbons. For example, an aliphatic group can be a t-butyl which contains as many as three PEG molecules on each of three carbon atoms (i.e., a total of 9 PEG molecules) and a reactive aldehyde moiety on the fourth carbon of the t-butyl. Examples of activated, branched PEG linkers are also described in U.S. Pat. Nos. 5,643,575, 5,919,455, and 5,932,462. One having ordinary skill in the art, in light of the present invention, can prepare modifications to branched PEG linkers as desired, e.g., addition of a reactive aldehyde moiety.

Methods for the preparation of linkers for use in the present invention are well known in the art, e.g., see U.S. Pat. Nos. 5,643,575, 5,919,455, and 5,932,462. Activated PEG-linkers, such as PEG-aldehydes, can be obtained from a commercial source, e.g., Shearwater Polymers, (Huntsville, Ala.) or Enzon, Inc. (Piscataway, N.J.).

B. Conjugation Reaction Between PEG and HSP70 Amino or Imino Group

The following schematic illustrates a reaction between an activated PEG aldehyde linker and an amino or imino group of an amino acid residue of one of the HSP70 monomers: PEG-R—CHO+$NH_2$-HSP70⇌PEG-R—CH=N-HSP70, where R is a $C_{1-11}$ alkyl and N is nitrogen of a reactive amino group on an amino acid residue of HSP70. In this reaction, the activated PEG covalently attaches to the HSP70 to form an imine linkage. Reduction of the imine linkage by the reducing agent, e.g., sodium cyanoborohydride (Sigma-Aldrich, St. Louis, Mo.) forms pegylated HSP70, as shown: PEG-R—CH=N-HSP70+$NaCNBH_3$→PEG-R—$CH_2$—NH-HSP70. Other reducing agents can be used instead of sodium cyanoborohydride in this reaction, including sodium borohydride, tertiary butyl amine borane, sodium triacetyl borohydide, dimethylamine borate, trimethylamine borate, and pyridine borate. Sodium cyanoborohydride is used in certain embodiments because it specifically reduces an imine linkage, which is formed between an aldehyde group of the activated PEG and amino group of the amino acid of HSP70.

As shown in the reactions, a Schiff base is formed during the preparation of PEG-HSP70. The concern that this intermediate, which is very difficult to separate from PEG-HSP70 and could lower the purity of the PEG-HSP70 if the intermediate accumulates in the reaction and is not reduced to the product, may be avoided by using higher concentrations of reducing agent, about 75:1 to 350:1 (e.g., Kinstler et al., Pharm. Res. 13:996-1002 (1996) and Chamow et al., Bioconjugate Chem. 5: 133-140 (1994)).

Various aqueous buffers can be used in the present method to catalyze the covalent addition of PEG to HSP70. The pH of a buffer used is from about 5.5 to 7.8, e.g., the pH is in a neutral range, e.g., from about 6.3 to 7.5. This neutral pH range would also increase the site-specific pegylation of HSP70 at the alpha amino group of the N-terminus versus other imino or amino groups of other amino acid residues, e.g., lysine or histidine. In certain embodiments, a buffers having a pKa close to neutral pH range is used, e.g., phosphate buffer.

The temperature range for preparing a PEG-HSP70 of the invention is from about 5° C. to 30° C. For example, in certain embodiments, the temperature is from about 18° C. to 25° C.

The pegylation reaction can proceed from 3 to 48 hours, e.g., 10 to 24 hours. The reaction can be monitored using SE (size-exclusion)-HPLC, which can distinguish HSP70, mono-PEG-HSP70 and di-PEG-HSP70 (i.e., pegylation occurs on two amino acid residues of HSP70), etc. At anytime when the desired HSP70 is obtained, the reaction can be terminated by adding glycine solution to quench any remaining activated PEG.

Conventional separation and purification techniques known in the art can be used to purify PEG-HSP70, such as size exclusion (e.g. gel filtration) and ion exchange chromatography.

It may be desirable to polish or resolve a population of PEG-HSP70 in a PEG-HSP70 composition prepared according to a method of the present invention. The polishing step separates less stable PEG-HSP70 (e.g. His-PEG-HSP70) from stable PEG-HSP70 (e.g. N-terminus-PEG-HSp70 or Lys-PEG-HSP70), and thus can achieve greater homogeneity of stable positional isomers, e.g., greater than 95% of a PEG-HSP70 composition. Less stable positional isomers of PEG-HSP70, e.g., histidine-PEG-HSP70, can be hydrolyzed during a polishing step. The population of PEG-HSP70 can be incubated in an aqueous buffer, e.g., a TRIS buffer (e.g., 10 to 300 mM, e.g., about 30 to 70 mM), at about pH 5.0 to 9.0, e.g., pH 7.0 to 8.0 at 15° C. at 35° C. overnight. Alternatively, the population of PEG-HSP70 can be treated with 0.05 to 0.4 M hydroxylamine HCl salt (pH about 6.5) at room temperature for 0.5 to 10 hours. Hydrolyzed HSP70 and PEG remnant can be removed from the population of stable PEG-HSP70 by a separation/purification step using, e.g., gel filtration or ion exchange chromatography.

In U.S. Pat. No. 5,985,265 the PEGylation of interferon using an aldehyde linker was accomplished at acidic pH 4.0 at 4° C. Conventional wisdom in the art teaches that for most activated PEG, as the reaction pH is increased under basic conditions pegylation occurs at more stable sites on the protein. For PEGylated IL-10 (U.S. Pat. No. 7,052,686), succinimidyl carbonate-PEG forms about 90% Lys-PEG-IL-10 (more stable) and about 10% His-PEG-IL-10 (less stable) at a reaction pH 8.8, and about 64% Lys-PEG-IL-10 and 36% His-PEG-IL-10 at a reaction pH 6.3.

C. Preparation of Cysteine Modified HSP70-PEG

In one embodiment, rhHSP70-PEG was prepared by using PEG-Maleimide-20 KDa reagent (Nanocs, N.Y., USA). The maleimide group reacted specifically with sulfhydryl groups when the pH of the reaction mixture was between pH 6.5 and 7.5; the result was formation of a stable thioether linkage that was not reversible (i.e., the bond cannot be cleaved with reducing agents). HSP70 has 5 cysteine groups in the following AA positions: 17, 267, 306, 574, and 603.

No cysteine thiols were known to participate in the formation of the intramolecular disulfide bonds and therefore all cysteines are potentially amenable to pegylation though in certain condition as Cys574 had been reported having a propensity for forming intermolecular disulfide bonds (Nemoto et al. 2006). From the structural consideration, Cys267, Cys306 could be buried in the middle of the protein and/or be masked by substrate making them less likely to be accessible. The Ellman test confirmed the presence of free thiol groups. However, when conducting the pegylation reaction in PBS buffer at pH 7.1, no changes in HPLC retention time were seen and subsequent SDS-PAGE gels did not reveal any reaction products but only a spot at 70 kDA for the unaltered HSP70.

After multiple trials, PEGylation only proceeded using denatured protein and the optimum conditions were in 6 M guanidine, whereas lower guanidine concentrations or using urea led to less efficient coupling. By varying the ratio of PEG-Maleimide the extent of cysteine pegylation was controlled, from an average of 1 to 5 PEG fragments per one protein molecule. Based on the HPLC data, a peak related to the starting protein vanishes when using a total of 50 eqv of PEG-maleimide. The final purification of HSP70-PEG is achieved by size exclusion chromatography in PBS at pH 7.4.

Pegylated protein products refolded rapidly when diluted in PBS or during a passage through the size-exclusion column. For in vivo experiments, pegylated products were concentrated using an Amicon membrane (cutoff 4 kDa) to a concentration of 0.5-2 mg/ml (as determined by micro BCA) and passed through a 0.22 micron filter. The biological activity of the HSP70-PEG molecules was confirmed by the ATPase test using a commercial kit (ENZO Life Sciences, Farmingdale, N.Y.). Different co-factors, e.g., HSP40 and modified albumins, have been reported to improve the test response; however, the most robust results were received in 1 mmol ADP.

ii. In Vivo Applications

Example 4

Application of the rhHSP70 for Increased Performance Capability Experienced During Intense Physical Exercise The goal of this experiment was to study the role of exogenous rhHSP70 in experimental model of intense physical exercise in healthy adult wild white male rats (180-220 g, "Rappolovo" animal facility) and its effect on increased endurance. rhHSP70 was used in two doses of 50 and 100 mcg per animal injected intraperitoneally in 1 ml of water. The experiment was conducted in 3 groups of animals: 6 animals (control, placebo injection), 6 animals (50 mcg HSP70), 6 animals (100 mcg HSP70). Experimental animals were pre-selected from the group that passed an initial fitness and training test: a daily run on a treadmill for 5 min repeated for 3 consecutive days (treadmill rate 20 m/min, attack angle 20°). The study treadmill test was run to exhaustion (termination of the running routine by an animal) for a total of 9 sessions that were repeated every second day, at the same time of the day. HSP70 was administered 5-6 min following the completion of the test for the first 6 sessions. The observed animal running time was used as a measure of endurance capability (FIG. 1, Table 1).

TABLE 1

Variations in performance (time of exercise to exhaustion) relative to the result of the first exercise session.

| Exercise Session No. | Days of Observation | Animal Groups | | |
|---|---|---|---|---|
| | | Control | HSP70, 50 mcg | HSP70, 100 mcg |
| 1 | 1 | 100 | 100 | 100 |
| 2 | 3 | 105.6 ± 5.9 | 108.6 ± 4.8 | 113.0 ± 4.0 |
| 3 | 5 | 106.2 ± 3.0 | 115.1 ± 5.9 | 119.0 ± 4.8* |
| 4 | 8 | 109.9 ± 4.2 | 124.1 ± 5.1* | 127.3 ± 5.2* |
| 5 | 10 | 81.2 ± 3.7 | 111.7 ± 3.5* | 113.9 ± 3.4* |
| 6 | 12 | 61.9 ± 4.4 | 104.2 ± 5.9* | 121.5 ± 5.3* |
| 7 | 15 | 55.6 ± 4.9 | 97.3 ± 3.0* | 114.6 ± 4.6* |
| 8 | 17 | 47.7 ± 4.0 | 62.2 ± 3.3* | 87.0 ± 4.0* |
| 9 | 19 | 46.7 ± 3.1 | 61.1 ± 4.1* | 82.2 ± 3.8* |

Note:
*statistically significant ($p \leq 0.05$) compared to control

A statistically significant differentiation in the endurance capability was seen during the 3rd training session: the control group and low-dose HSP70 animals were shown to have results similar to the training session No. 1, whereas the high-dose HSP70 animals demonstrated improved endurance (FIG. 1). In all the subsequent training sessions, the HSP70-treated animal outperformed a control group in a dose-dependent manner.

Starting from the training session No. 5, the performance/endurance in all groups began to decrease. However, the trend was slower in the HSP70-treated animals. After termination of the HSP70 administration following the training session No. 6, the endurance capability has further decreased, however, in each training session the animal receiving HSP70 outperformed untreated animals, by as much as 35.5% in the 100 mcg group in the last training session No. 9.

As a result of the exhaustion following the exercise on the day 19, the control group demonstrated increased levels of blood proteins, creatinine, as well as sodium and potassium as compared with both treated groups (Table 2). Additionally, treated animals displayed decreased activity of the creatinine kinase and lactate dehydrogenase (LDG) that may indicate cytoprotective properties of the HSP70. Importantly, we detected no anabolic effects of HSP70—there was no additional body mass increase in treated group as compared to the control group though all animals demonstrated slightly elevated body mass at the end of the experiment.

TABLE 2

Blood biochemistry results following completion of the study (day 19).

| Test | Units | Animal Groups | | |
|---|---|---|---|---|
| | | Control | HSP70, 50 mcg | HSP70, 100 mcg |
| Proteins | g/L | 72.5 ± 1.7 | 63.6 ± 1.1* | 66.0 ± 1.6* |
| Creatinine | mmol/L | 67.7 ± 3.1 | 52.0 ± 3.5* | 56.3 ± 1.4* |
| Uric Acid | mmol/L | 9.1 ± 1.2 | 8.6 ± 0.7 | 9.7 ± 0.4 |
| Glucose | mmol/L | 7.2 ± 0.5 | 6.6 ± 0.2 | 6.6 ± 0.8 |
| $K^+$ | mmol/L | 6.6 ± 0.3 | 6.8 ± 0.2 | 7.3 ± 0.2 |
| $Na^+$ | mmol/L | 149.4 ± 0.9 | 144.2 ± 0.5* | 145.2 ± 0.5* |
| $Ca^{2+}$ | mmol/L | 2.50 ± 0.03 | 2.46 ± 0.05 | 2.46 ± 0.01 |
| $Cl^-$ | mmol/L | 112.2 ± 0.9 | 107.8 ± 1.2* | 109.8 ± 0.3* |
| Creatinine kinase | IU/L | 13368.0 ± 455.3 | 10668.4 ± 312.0* | 8954.5 ± 826.4* |
| LDG | IU/L | 6245.7 ± 260.4 | 3146.8 ± 227.2* | 2407.8 ± 241.2* |

Note:
*statistically significant (p ≤ 0.05) compared to control

Microscopy Analysis

Figure 2:
FIG. 2 depicts muscle electron microscopy (×15000) from the control (untreated) animal. Clearly visible is myofibrils separation and edema, capillary edema, and damaged erythrocytes (shadows) as manifestation of the rhabdomyolysis. An activated podocyte is located in the upper left corner.
Figure 3:
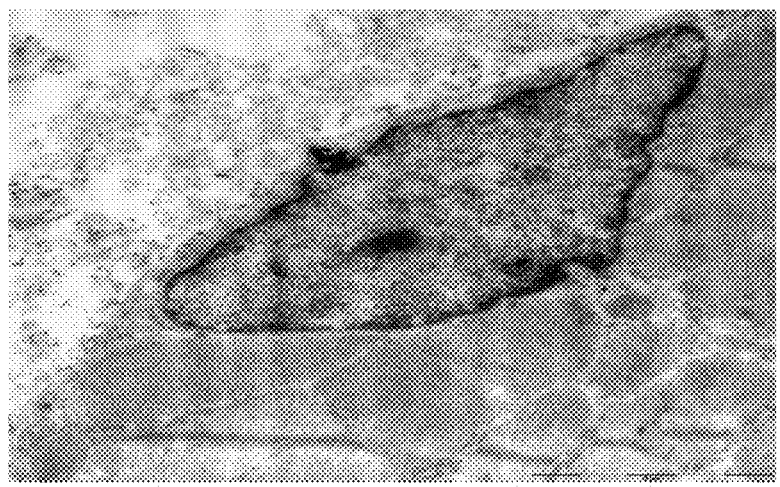
FIG. 3 depicts muscle electron microscopy (×15000) from the treated animal (HSP70, 100 mcg). The view is dominated by an activated satellite cell with a large euchromatin-rich nucleus.
Figure 4:
FIG. 4 depicts muscle electron microscopy (×15000) from the treated animal (HSP70-PEG, 100 mcg). The view is dominated by an activated satellite cell and numerous mitochondria.
Figure 5:
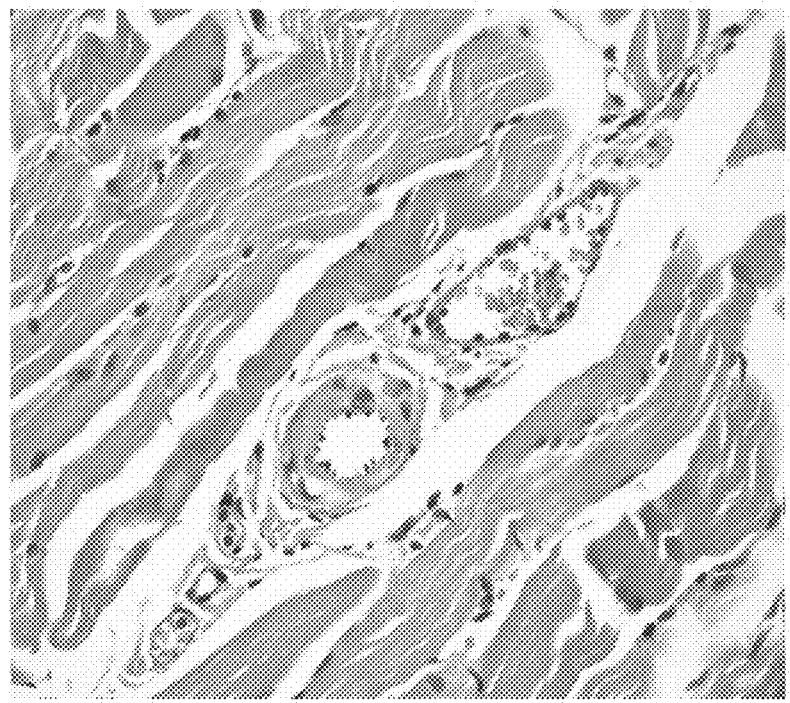
FIG. 5 depicts muscle optical microscopy (×400) from the treated animal (HSP70, 100 mcg). Zones of the neoangiogenesis are clearly visible with partial myofibrils separation.
Figure 6:
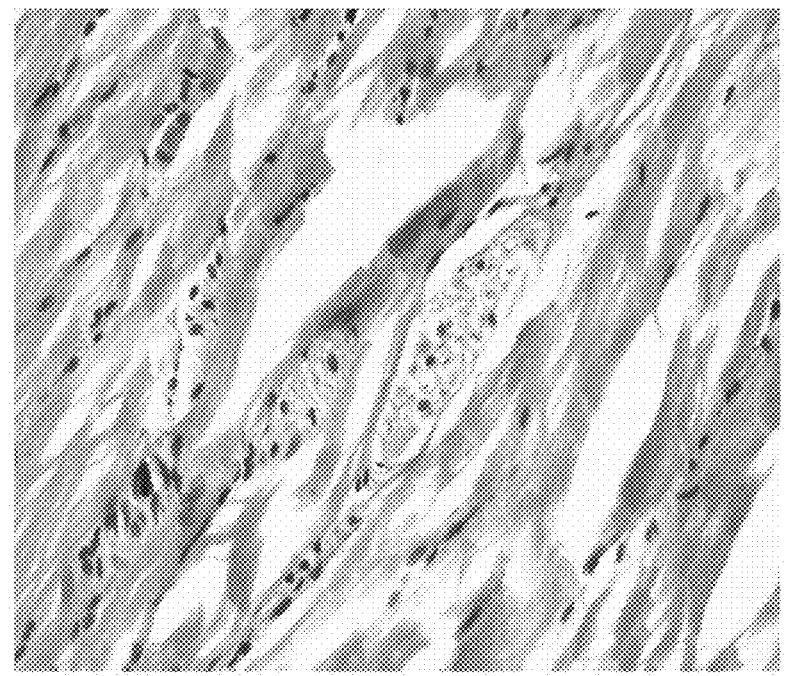
FIG. 6 depicts muscle optical microscopy (×400) from the treated animal (HSP70-PEG, 100 mcg). Zones of the neoangiogenesis with large lymphocytes are clearly visible with partial myofibrils separation.

To confirm the findings from the physiological functional testing and blood biochemistry, a limb muscle biopsy was conducted in the sacrificed animals following a completion of the study. Transmission electron microscopy was carried out on a JEOL 110 CX and Hitachi H-300 electron microscopes using samples fixed by 2.5% glutaric aldehyde with subsequent treatment in PBS solution of the osmium tetraoxide and dewatering in alcohol/acetone (FIG. 2-4). Tissue slices were generated using Ultracut-Reichert microtome. The Mallory staining for optical microscopy was done with eosin and hematoxylin (FIG. 5,6).

In all the groups structural alterations were detected indicative of a muscle dystrophy, rhabdomyolysis and inflammation that was less pronounced in the treated groups. An activation of angiogenesis is known to be strongly associated with muscle regeneration (Borselli et al., 2010), with a capillary network being an important indication of the recovery processes. Correspondingly, in HSP70-treated animals, a significant dose-dependent increase was found in the density of the capillary vessels, by 170-330%, from 275/mm$^2$ in the control group to 907/mm$^2$ in the high-dose HSP70 treated group (Table 3).

Additionally, staining was performed for the satellite cells, an adult stem cell population associated with myofibers and localized within the basal lamina of the muscle fibers that are believed to be primarily responsible for muscle regeneration (Wagers et al., 2005). A 6-8 times increase was observed in the density of the satellite cells in the HSP70-treated versus untreated animals (Table 3).

TABLE 3

Capillary density and satellite cells count following completion of the exercise study.

| Parameter | Animal Groups | | |
|---|---|---|---|
| | Control | HSP70 (100 mcg) | HSP70-PEG (100 mcg) |
| Capillary density (per mm$^2$) | 275.0 ± 21.2 | 907.5 ± 37.4* | 990 ± 37.4* |
| Satellite cells (% control) | 100 | 680.2 ± 150.3* | 840.1 ± 170.4* |

Note:
*statistically significant (p ≤ 0.05) compared to control

Example 5

Application of the rhHSP70-PEG for Increased Performance Capability Experienced During Intense Physical Exercise The goal of this experiment was to study the role of exogenous rhHSP70-PEG in experimental model of intense physical exercise in healthy adult wild white male rats (180-220 g, "Rappolovo" animal facility) and its effect on increased endurance. rhHSP70-PEG was used in a dose of 100 mcg per animal injected intraperitoneally in 1 ml of water. The experiment was conducted in 3 groups of animals: 6 animals (control, placebo injection), 6 animals (100 mcg HSP70), 6 animals (100 mcg HSP70-PEG). Experimental animals were pre-selected from the group that passed an initial fitness and training test: a daily run on a treadmill for 5 min repeated for 3 consecutive days (treadmill rate 20 m/min, attack angle 20°). The study treadmill test was run to exhaustion (termination of the running routine by an animal) for a total of 10 sessions that were repeated every day, at the same time of the day. HSP70 and HSP70-PEG were administered 5-6 min following the completion of the test on the daily basis. The observed animal running time was used as a measure of performance capability (Table 4).

There was no significant difference between the groups in the first five training sessions. After that, a ca. 30% drop was observed in the exercise time for the control and subsequent decrease in the follow-up sessions, to ca. 50% of the capacity at the end of the experiments. In contrast, treated groups displayed a gradually increased performance reaching 115-125% as compared to the beginning of the study. HSP70-PEG showed a statistically significant performance improvement over HSP70. This observation was corroborated by the higher density of the capillary vessels and satellite cells count (Table 3).

Notably, we again detected no anabolic effects of HSP70 or HSP70-PEG (Table 5)—there was no additional body mass increase in treated group as compared to the control group though all animals demonstrated slightly elevated body mass at the end of the experiment (Table 5).

TABLE 4

Variations in performance (time of exercise to exhaustion) relative to the result of the first exercise session for HSP70-PEG.

| Exercise session/day | Animal Groups | | |
|---|---|---|---|
| | Control | HSP70 (100 mcg) | HSP70-PEG(100 mcg) |
| 1 | 100 | 100 | 100 |
| 2 | 105.3 ± 6.0 | 104.9 ± 6.8 | 103.4 ± 1.2 |
| 3 | 109.9 ± 5.4 | 103.1 ± 6.6 | 104.6 ± 7.7 |
| 4 | 106.8 ± 8.5 | 119.1 ± 2.9 | 109.9 ± 5.5 |
| 5 | 101.7 ± 6.6 | 112.9 ± 4.8 | 115.0 ± 1.8 |
| 6 | 86.9 ± 9.1 | 115.9 ± 5.2* | 117.0 ± 2.1* |
| 7 | 56.1 ± 7.9 | 123.8 ± 3.8* | 121.2 ± 5.6* |
| 8 | 68.7 ± 4.1 | 119.2 ± 2.8* | 123.4 ± 3.6* |
| 9 | 60.2 ± 1.7 | 117.0 ± 4.6* | 125.1 ± 1.9* |
| 10 | 54.8 ± 5.3* | 115.6 ± 3.6* | 124.3 ± 6.7* |

Note:
*statistically significant ($p \leq 0.05$) compared to control

TABLE 5

Body mass change (g) in the course of exercise routine.

| Exercise Session | Animal Groups | | |
|---|---|---|---|
| | Control | HSP70-PEG (100 mcg) | HSP70-PEG (100 mcg) |
| 1 | 161.7 ± 6.9 | 162.2 ± 7.7 | 161.0 ± 7.8 |
| 2 | 166.3 ± 7.7 | 184.3 ± 7.1 | 179.3 ± 3.5 |
| 3 | 168.0 ± 7.8 | 187.0 ± 7.1 | 183.0 ± 3.9 |
| 4 | 171.8 ± 8.2 | 190.0 ± 6.8 | 187.3 ± 4.5 |
| 5 | 174.3 ± 8.2 | 189.8 ± 7.4 | 189.3 ± 4.1 |
| 6 | 174.2 ± 8.7 | 189.8 ± 6.0 | 188.0 ± 2.9 |
| 7 | 174.8 ± 8.9 | 192.5 ± 5.6 | 189.3 ± 3.6 |
| 8 | 178.5 ± 8.7 | 195.2 ± 4.8 | 184.0 ± 4.3 |
| 9 | 182.5 ± 8.8 | 198.2 ± 4.6 | 195.0 ± 3.7 |
| 10 | 182.2 ± 8.6 | 196.0 ± 4.2 | 199.7 ± 4.1 |

Example 6

Clinical Use of HSP70 for Treatment of the Acquired Muscle Myopathy

Figure 7:
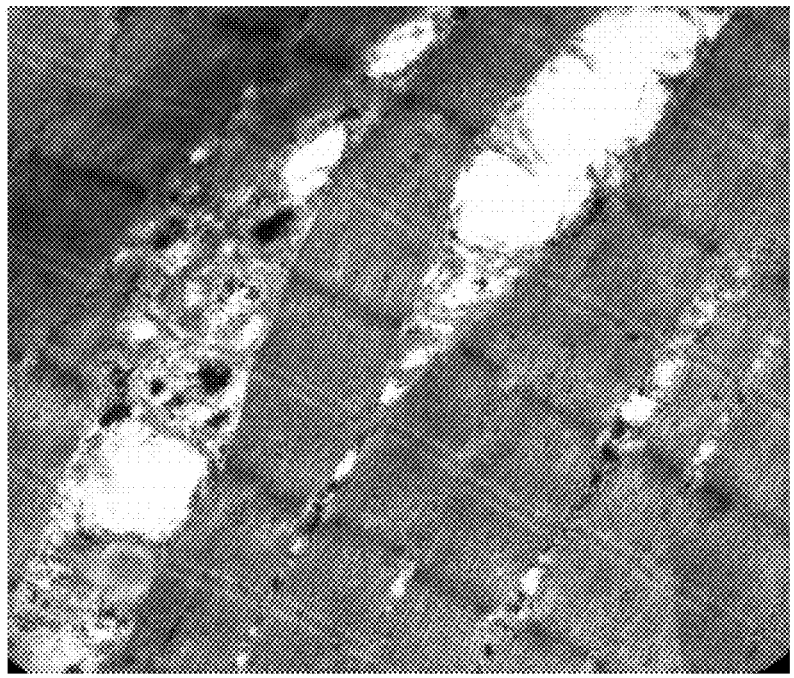
FIG. 7 depicts muscle electron microscopy (×15000) of the patient before the treatment with HSP70. Muscle damage is manifested in a formation of the vacuoles, delamination of the myofibrils and formation of the glycogen aggregates in between the myofibrils.

Subject X, a 62 year old human patient suffered from a significant body mass loss (35 kg over a period of 1 year), muscle atrophy of the lower extremities and upper body, decrease in the muscle power and endurance, muscle contractures. Electron microscopy (FIG. 7) of the biopsy from musculus brachialis and gastrocnemius revealed significant rhabdomiolysis, mitochondrial damage with a formation of numerous vacuoles, and reduction in the number of satellite cells. The clinical diagnosis was established in Saint Petersburg (Russia) Military Medical Academy as an acquired mitochondrial myopathy and resulting cachexia.

HSP70 was then administered IV, 0.5 mg per dose over a period of 7 days.

Figure 8:
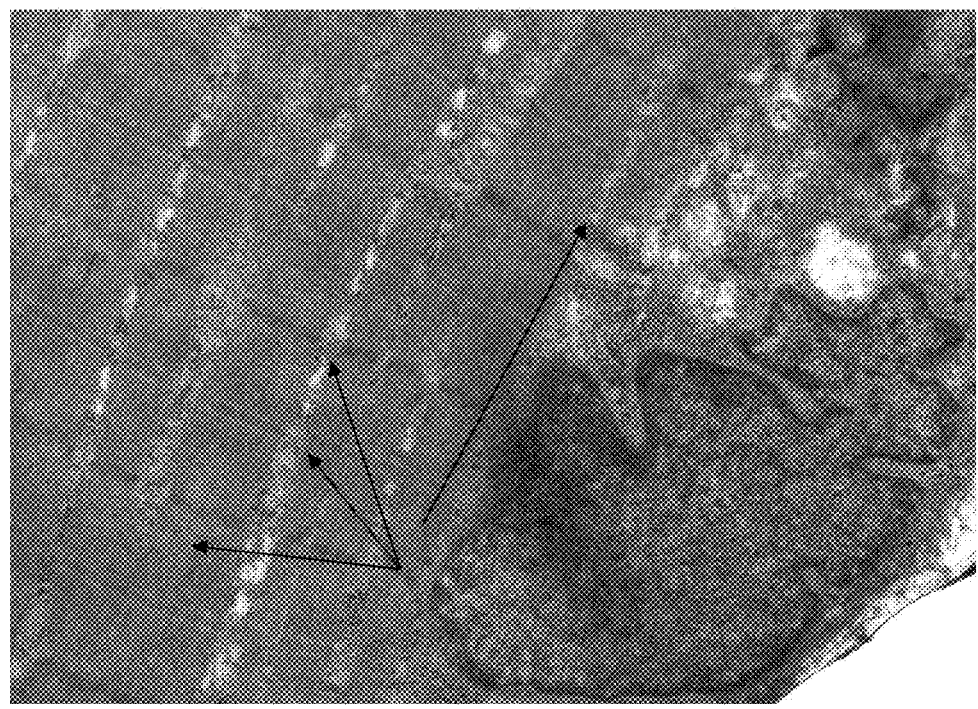
FIG. 8 depicts muscle electron microscopy (×15000) of the patient after the treatment with HSP70. Muscle regeneration is manifested in improved cross-section, and activated myocyte nuclear function.

Analysis following the 6 weeks subsequent to the last administration of HSP70 showed that the patient's body mass had increased by 6.5 kg, which was associated with increased muscle strength. In addition, the electron microscopy (FIG. 8) revealed significant reduction in the myofibril delamination and their improved cross-section, restoration of the mitochondrial structure and activation of the myocyte nuclear function.

B. Establishment of Activity Profiles of HSP70 Fusion Proteins

HSP70 has been shown to act to treat HSP70 related disease and disorders, and to increase performance, alleviate fatigue syndrome, or treat muscle damage or muscle degeneration. The following experimentals demonstrate that HSP70 fusion proteins are active and show improved properties over HSP70 alone in certain areas.

Example 7

Expression and Biological Activity of the HSP70-Fc Fusion Protein

Expression and Purification

HSP70-Fc fusion protein (full sequence is shown in SEQ ID NO: 1) conjugated at the N-terminus of human HSP70 with an Fc fragment of the human IgG1 through a linker consisting of a hinge region of the Fc fragment and a TEV sequence (ASGAGSTTENLYFQGGS) has been expressed in the human embryonic cell line 239 (ATCC Catalog No. CRL-1573). The expression-ready clone of human HSP70 was purchased from OriGene (Catalog No. SC116766; NM_005345.4; HuHSP70) and consisted of the vector plasmid pCMV6-XL5 (4.5 Kb; ampicillin resistant) and the insert (HuHSP70, 2.5 Kb). The expressed HSP70-Fc protein was secreted and was purified according to the following process.

Figure 9:
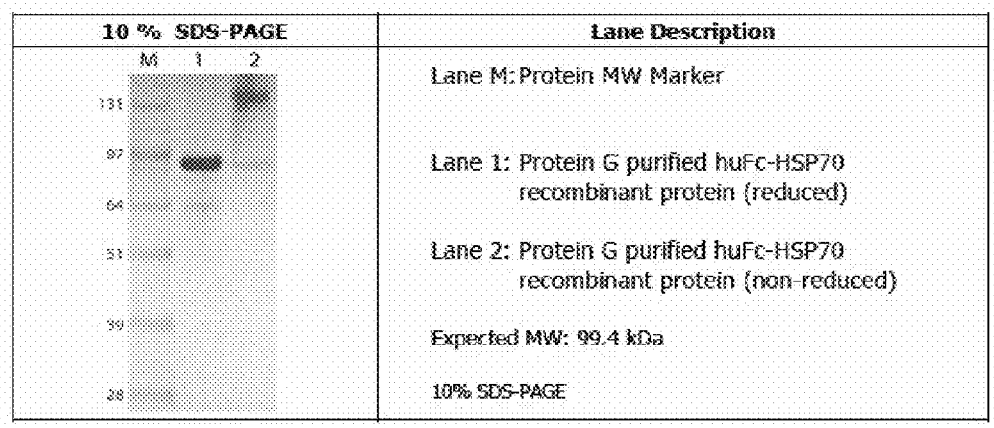
FIG. 9 depicts the SDS-PAGE of HSP70-Fc.

Protein G resin was washed three times with 10-20 column volumes of ice-cold PBS, pH 7.4. Protein sample was then loaded onto the resin column that had a binding capacity of ca. 20 mg/mL of the Fc-fusion protein. The column was washed twice with 10-20 column volumes of PBS to remove unbound and non-specifically bound proteins. Washes with PBS were continued until the absorbance at 280 nm reached background levels (A<0.2). The column-bound protein was eluted using an elution buffer at pH 2.7 (50 mM glycine-based, Thermo Scientific, Catalog No. 21004), while collecting 1 ml fractions into the tubes containing a neutralizing buffer (1 M Tris, pH 9.0). Purified protein (SEQ ID NO. 1) was then dialyzed against two 1 L changes of 1×PBS (pH 7.2) over a 24 h period. Various concentrations of the protein were run on a 4-12% Bis-Tris NuPAGE gel and the results are shown in FIG. 9.

In Vitro Biological Activity

Figure 10:
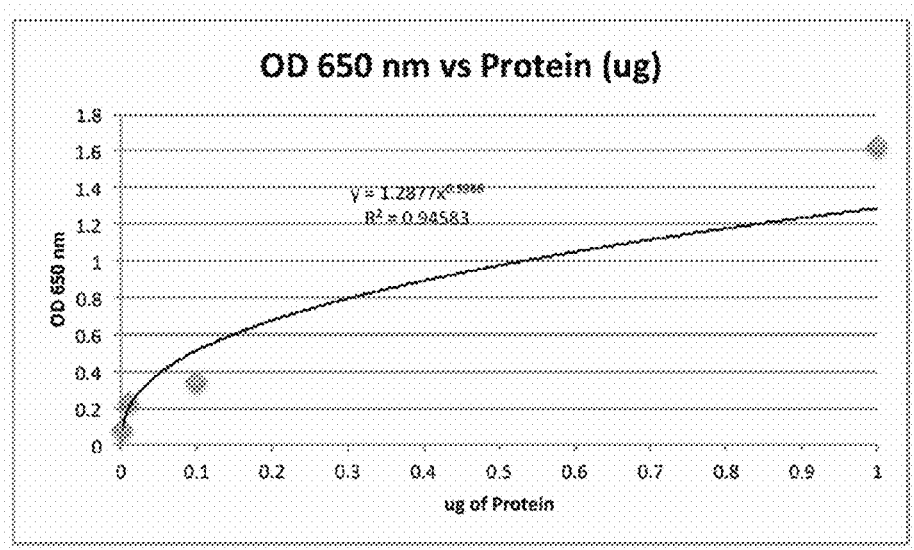
FIG. 10 depicts the ATPase activity results for the HSP70-Fc fusion protein. Increasing amounts of protein (0.001 µg to 1 µg) of protein were added to the assay mixture. Reaction was stopped after 45 minutes and Pi detected using malachite green.

We characterized the HSP70-Fc fusion protein for its ATPase activity, which is a major attribute of biological function. Different amounts of protein were incubated in an assay mixture consisting of 50 mM Tris (pH 7.5), 2.5 mM $MgCl_2$, and 0.5 mM ATP. The assay was carried out at 37° C. for 20 min and the production of free inorganic phosphate (Pi) measured using the commercial ATPase Assay Kit (Innova Biosciences, Catalog No. Ca601-0121). The results are presented in FIG. 10. As can be seen, the assay was linear only at very low concentration of protein (0-0.001 micrograms of protein). The protein showed a very high level of the ATPase activity (≥640 μM Pi/hr/μg protein).

PK Properties

Pharmacokinetic properties of HSP70-Fc protein conjugate were investigated in rats. 10 female CD rats (225-250 g) with an implanted jugular vein catheter (JUGVEIN, Charles River, Cat. No. 24100511) were used in the study. 4 rats were injected with a bolus of 100 microg of HSP70 in PBS, 4 rats were injected with 100 microg of HSP70-Fc, 2 rats served as a control group and received PBS. Blood samples were drawn at time points 15, 30 min, 1, 2, 4, and 6 hours. Concentration of HSP70 in plasma was determined using a commercial ELISA assay (Enzo Life Sciences, Catalog No. ADI-EKS-715). HSP70 was undetectable at 4 h whereas HSP70-Fc fusion protein was present at 30% level of the initial dose and at 25% level at 6 h time point.

Example 8

Application of the HSP70-Fc Fusion Protein for Alleviation of Stroke in the Mouse Model of the Ischemia-Reperfusion Injury The experimental design of the stroke study was as described in the literature (D. N. Atochin et al., The phosphorylation state of eNOS modulates vascular reactivity and outcome of cerebral ischemia in vivo, J. Clin. Invest., 117 (2007) 1961). Specifically, a filament model of middle cerebral artery (MCA) occlusion was used. Mice were anesthetized with 1.5% isoflurane in a mixture of 30% $O_2$ and 70% $N_2O$. Body temperature was maintained at 37° C. using a thermostatic heating blanket (FHC). A flexible fiber optic probe (Perimed) was affixed to the skull over the brain area supplied by the MCA (2 mm posterior and 6-7 mm lateral to bregma) for relative blood flow measurements by laser Doppler flowmetry. Baseline cerebral blood flow values were measured before internal carotid artery ligation and MCA occlusion and considered to be 100% flow. MCA occlusion was caused by inserting an 8-0 nylon filament (Doccol Corp.) covered by silicon into the internal carotid artery and advancing it to the origin of the MCA. Ischemia was confirmed by reduction in blood flow to less than 20% of control values, measured by laser Doppler flowmetry. Reperfusion was confirmed by Doppler after withdrawal of the filament.

Determination of the Infarct Size.

Infarct size was determined by staining with 2,3,5-triphenyltetrazolium chloride (TTC) (Sigma-Aldrich). Brains were cut into 2-mm-thick coronal sections using a mouse brain matrix (RBM-200C; Activational Systems), stained with 2% TTC for 1 hour at 37° C. in the dark, and photographed with a digital camera. Sections were analyzed using an image analysis system (MCID M4; Imaging Research).

Infarct sizes were determined by the indirect method, which corrects for edema (contralateral hemisphere volume minus volume of nonischemic ipsilateral hemisphere).

Neurologic Scoring.

Mice were examined for neurologic deficits 23 hours after MCA occlusion using a 5-point scale. Normal motor function was scored as 0, flexion of the contralateral torso and forearm on lifting the animal by the tail as 1, circling to the contralateral side but normal posture at rest as 2, leaning to the contralateral side at rest as 3, and no spontaneous motor activity as 4.

In a group of 10 animals, the animals were administered (by IP injection) 10 microg of HSP70 to 5 mice and 10 microg of HSP70-Fc to 5 mice, 30 min following an MCA occlusion, and observed the mice for 48 h. All animals survived the experiment. The infarct volume of the HSP70-Fc treated animals was 50% less then those received HSP70. The neurological scoring was lower, in average, by 1.2 points in the HSP70-Fc-treated group, from 3.4 to 2.2.

Example 9

Application of the HSP70-Fc Fusion Protein for Increased Performance Capability Experienced During Intense Physical Exercise The goal of this experiment was to study the role of exogenous HSP70-Fc fusion protein in experimental model of intense physical exercise in healthy adult wild white male rats (180-220 g, "Rappolovo" animal facility) and its effect on increased endurance. HSP70-Fc was used at 50, and HSP70 at 100-microgram dose per animal, injected intraperitoneally in 1 ml of the PBS solution. The experiment was conducted in 3 groups of animals: 6 animals (control, placebo injection), 6 animals (100 microgram HSP70), 6 animals (50 microgram HSP70-Fc). Experiments participants were pre-selected from the group that passed an initial fitness and training test: a daily run on a treadmill for 5 min repeated for 3 consecutive days (treadmill rate 20 m/min, attack angle 20°, electroshock plate mounted at the base). The study treadmill test was design as "run to exhaustion" (termination of the running routine by an animal) for a total of 10 sessions that were repeated every day, at the same time of the day. The animals were kept on a regular diet ad libitum and then sacrificed on the day 11 of the experiment. HSP70 and HSP70-Fc were administered daily, 5-6 min following a completion of the test. The observed animal running time was used as a measure of endurance capability (Table 6). A total duration of the exercise for the individual animals spanned from 8 to 25 min.

TABLE 6

Variations in performance (time of exercise to exhaustion) relative to the results of the first exercise session, (%).

| Exercise Session No. (day) | Control | HSP70 | HSP70-Fc |
|---|---|---|---|
| 1 | 100 | 100 | 100 |
| 2 | 105 | 88 | 95 |
| 3 | 99 | 119 | 125 |
| 4 | 106 | 104 | 105 |
| 5 | 99 | 105 | 103 |
| 6 | 104 | 100 | 94 |
| 7 | 78 | 105 | 104 |
| 8 | 68 | 107 | 107 |
| 9 | 65 | 105 | 100 |
| 10 | 64 | 108 | 104 |

We observed a significant drop in the endurance in the control group starting on the day 7, with an exercise time rapidly reduced to 64% (of the day 1 capability) at the end of the experiment, whereas the groups treated with HSP70 and HSP70-Fc stayed at the same or slight better levels. Importantly, we detected no anabolic effects of both HSP70 and HSP70-Fc—there was no additional body mass increase in treated groups as compared to the control group.

As a result of the exhaustion following the exercise, on the day 11, the control group demonstrated increased levels of blood proteins, creatinine, as well as sodium and potassium as compared with both treated groups. Additionally, treated animals displayed decreased activity of lactate dehydrogenase (LDG) and a particularly significant drop in creatinine kinase, by 35% for HSP70, and as much as 85% as compared to the control for HSP70-Fc that indicate pronounced cytoprotective properties of the heat shock proteins (Table 7).

TABLE 7

Blood biochemistry results following completion of the exercise study (day 11).

| | Animal Group | | |
|---|---|---|---|
| Test type | Control | HSP70 | HSP70-Fc |
| Creatinine kinase, IU/l | 8017 ± 310 | 5201 ± 260.0* | 1312 ± 124* |
| LDG, IU/l | 754 ± 91 | 601 ± 78* | 600 ± 82* |

Note:
*statistically significant (p ≤ 0.05) compared to control

Microscopy Analysis

To confirm the findings from the physiological functional testing and blood biochemistry, a limb muscle biopsy was conducted on the sacrificed animals following a completion of the study. Transmission electron microscopy was carried out using a JEOL 110 CX microscope. Tissue slices were generated on a Ultracut-Reichert microtome. The Mallory staining for optical microscopy was done with eosin and hematoxylin.

In all the groups structural alterations were detected indicative of a muscle dystrophy, rhabdomyolysis and inflammation that was significantly less pronounced in the treated groups. An activation of angiogenesis is known to be strongly associated with muscle regeneration (Borselli C, Storrie H, Benesch-Lee F, Shvartsman D, Cezar C, Lichtman J W, Vandenburgh H H, Mooney D J. Functional Muscle Regeneration with Combined Delivery of Angiogenesis and Myogenesis Factors. Proc. Natl. Acad. Sci. U.S. A. 2010, 107(8):3287-92), with a capillary network being an important indication of the recovery processes. Correspondingly, in the HSP70-treated animals, we found a significant increase in the density of the capillary vessels, by 330%, from 275/mm$^2$ in the control group to 907/mm$^2$. We observed further increase in the capillary density in the HSP70-Fc treated group, to 1317/mm$^2$, now almost 5 times higher than controls (Table 8).

Additionally, staining was performed for the satellite cells, an adult stem cell population associated with myofibers and localized within the basal lamina of the muscle fibers that are considered to be primarily responsible for muscle regeneration (Wagers A J, Conboy I M, Cellular and Molecular Signatures of Muscle Regeneration: Current Concepts and Controversies in Adult Myogenesis, Cell 2005, 122:659-667). A 680% increase was observed in the density of the satellite cells in the HSP70-treated versus untreated animals, whereas HSP70-Fc again showed a superior performance, with a 920% increase in the satellite cells (Table 8).

TABLE 8

Capillary density and satellite cells count following completion of the exercise study.

| | Animal Groups | | |
|---|---|---|---|
| Parameter | Control | HSP70 | HSP70-Fc |
| Capillary density (per mm$^2$) | 275.0 ± 21.2 | 907.5 ± 37.4* | 1317.6 ± 54.6* |
| Satellite cells (% control) | 100 | 680.2 ± 150.3* | 920.1 ± 165.7* |

Note:
*statistically significant (p ≤ 0.05) compared to control

Example 10

Application of the HSP70-Fc Fusion Protein for Treating Melanoma

An efficacy of the HSP70-Fc fusion protein as a potential cancer therapy has been investigated in a B16 mouse model of melanoma (W. W. Overwijk, N. Restifo, B16 as a Mouse Model for Human Melanoma, Curr. Prot. Immunol., 2001, Ch. 20.1). Briefly, 36 C57BL 10-12 weeks old female mice (weight 20-26 g, Puschino breeding facility, Russia) received a subcutaneous injection of 1×10$^6$ B16 cells (Institute of Oncology, St. Petersburg, Russia). Tumors became visible in 10-12 days. Tumor growth was associated with a reduced mass, limited mobility and grooming.

In the control group (12 mice), untreated animals started perishing on the day 22 upon tumor cells injection, with an average life span of 28.2 days. In the treated groups, 12 animals received an intratumoral injection of HSP70 (50 microgram in 100 microl PBS) and 12 animals HSP70-Fc (50 microgram in 100 microl PBS) on the day 12, 14, and 16 and displayed significant tumor growth reduction and survival time, as well as reduction in a number of the metastatic animals and related metastatic formations per animal (Table 9). An average tumor volume at different days of disease progression is shown in Table 10. A more pronounced therapeutic effect was observed for HSP70-Fc as compared to HSP70. The blood levels of IL-6 showed a large reduction as compared to untreated animals, with HSP70-Fc outperforming HSP70.

Histological studies on the developing melanoma tumors in C57BL mice injected with HSP-70 and Hsp70-Fc also demonstrated an extensive infiltration of the tumor site with T lymphocytes and macrophages, whereas no mononuclear cell infiltrates were observed in the control group. Overall, an intratumoral injection of heat shock proteins elicits a protective immune response against the primary tumor and immune-mediated destruction of metastatic cells expressing tumor antigens.

TABLE 9

Tumor development parameters in the melanoma B16 mouse model of HSP70-Fc

| Group | S** | Tumor growth reduction (% vs. control, by day 22) | Survival time increase, % | Metastatic mice, % | Metastatic formations, per animal | IL-6, pg/l |
|---|---|---|---|---|---|---|
| Control | 3478 ± 512 | n/a | n/a | 100 | 23.6 ± 2.5 | 155 ± 19 |
| Hsp70 | 2073 ± 617 | 74* | 91.2 | 62* | 9.2 ± 2.7 | 60 ± 10 |
| Hsp70-Fc | 1475 ± 639 | 122* | 134.7 | 47* | 5.3 ± 2.9 | 37 ± 15 |

*p > 0.05 compared to control;
**AUC for the tumor growth kinetics curve

TABLE 10

Melanoma size (mm³) at different days after tumor cells injection.

| | Day | | | | | |
|---|---|---|---|---|---|---|
| | 12 d | 14 d | 16 d | 18 d | 20 d | 22 d |
| Control | 68 ± 38 | 114 ± 42 | 185 ± 48 | 287 ± 56 | 499 ± 61 | 847 ± 109 |
| Hsp70 | 77 ± 55 | 85 ± 45* | 92 ± 44* | 139 ± 62* | 226 ± 78* | 398 ± 104* |
| Hsp70-Fc | 82 ± 59 | 92 ± 47* | 98 ± 46* | 120 ± 59* | 213 ± 81* | 309 ± 118* |

*p > 0.05 compared to control

Example 11

Preparation of the HSP70-Fc Fusion Proteins Radiolabeled with I-123, I-124, I-125 and I-131 and Use of the Radiolabeled Constructs for Tumor Imaging and Treatment Radiolabeling Hsp70-Fc fusion proteins radiolabeled with I-123, I-124, I-125 and I-131 were prepared by iodination at tyrosine and histidine residues using iodo-beads as described in (T. N. M. Schumacher, T. J. Tsomides "In Vitro Radiolabeling of Peptides and Proteins", Current Protocols in Protein Science, 2001). Iodo-beads are nonporous polystyrene beads with an immobilized oxidizing agent (N-chlorobenzenesulfonamide) capable of converting iodide to its reactive form.

The iodo-beads (Pierce Protein Biology Products) were washed with 1 ml of 0.1 M sodium phosphate, dried on the filter paper and re-suspended in 0.5 ml of the same buffer. $Na^{123}I$, $Na^{124}I$, $Na^{125}I$ or $Na^{131}I$ were added to the beads and the reaction mixture agitated for 5 min followed by addition of HSP70-Fc and agitation for another 30 min. The reaction product is purified by a passage through a Sep-Pak C18 cartridge eluting with a 1:1 mixture of water and acetonitrile. The labeled protein is then recovered using a Speedvac evaporator. The radioactive iodine incorporation was at 90-92% and protein recovery at 88-90%.

In Vivo Biodistribution and Imaging Studies

The biodistribution of $^{123}I$-HSP70-Fc was studied in 20 C57BL female mice bearing a B16 murine melanoma. 12 days after tumor cell injection, $^{123}I$-HSP70-Fc (0.37-0.74 MBq, 100 µL in PBS) was injected via the tail vein. At defined times after injection (1, 3, 6, 24, and 48 h), smaller groups of mice (n=4) were sacrificed. Selected organs were weighed and their radioactivity measured using a gamma-counter. The uptake was expressed as the percentage of the injected dose per gram tissue (% ID/g tissue). The results are presented in Table 11 and show a preferential accumulation of the $^{123}I$-HSP70-Fc in the tumor. At 24 h, as much as 9.9% of the uptake is in the melanoma, whereas the second major organs of accumulation are liver and kidney, at 0.8%, a more then 12 times enhancement. These results have been corroborated by a whole-body single photon emission computed tomography (SPECT) study.

TABLE 11

$^{123}I$-HSP70-Fc uptake (% ID/g) in B16 melanoma mice model

| Time (h) | Tumor | Liver | Kidney | Lung | Heart | Blood |
|---|---|---|---|---|---|---|
| 1 | 12.7 ± 2.5 | 16.5 ± 2.1 | 8.5 ± 1.3 | 5.1 ± 0.7 | 3.3 ± 0.6 | 1.4 ± 0.2 |
| 3 | 22.1 ± 4.1 | 15.3 ± 2.8 | 7.2 ± 1.2 | 4.3 ± 0.4 | 2.4 ± 0.4 | 0.8 ± 0.3 |
| 6 | 26.0 ± 2.5 | 11.0 ± 1.8 | 6.5 ± 0.7 | 3.4 ± 0.4 | 1.6 ± 0.3 | 0.4 ± 0.2 |
| 24 | 9.9 ± 2.7 | 0.81 ± 0.22 | 0.85 ± 0.15 | 0.33 ± 0.10 | 0.14 ± 0.04 | 0.07 ± 0.02 |
| 48 | 5.3 ± 1.2 | 0.24 ± 0.07 | 0.38 ± 0.07 | 0.10 ± 0.02 | 0.07 ± 0.01 | 0.02 ± 0.01 |

In Vivo Efficacy Studies

A biodistribution study of $^{123}I$-HSP70 provided a valuable guideline for using $^{131}I$-labeled protein for therapeutic application in melanoma mice model. We selected to administer a dose of 37 MBq that should have allowed a delivery of 49 Gy to the tumor, in line with commonly used efficient doses reported in the literature. $^{131}I$-HSP70 and $^{131}I$-HSP70-Fc fusion protein were administered intravenously twice, at days 12 and 16 after tumor cell injections (2×18.5 MBq), in the groups of 5 mice each. For comparison, two groups of mice (5 animals each) received two IV injections (50 microgram) of non-radiolabeled HSP70 and HSP70-Fc fusion protein at the same days. The results of the study are summarized in the Table 12. Immunoradiotherapy using $^{131}I$-labeled HSP70 and HSP70-Fc resulted in significant reduction in tumor growth, increased survival time and associated decrease in a population of the metastatic animals as well as number of the metastatic formation per animal. In comparison, non-labeled HSP-70 and HSP70-Fc proteins displayed less pronounced effects. Overall, $^{131}I$-HSP70-Fc fusion protein had a superior performance in the group.

TABLE 12

Tumor development parameters in the radioimmunotherapy melanoma B16 mouse model

| Group | S** | Survival time increase, % | Metastatic mice, % | Metastatic formations, per animal |
|---|---|---|---|---|
| Control | 3478 ± 512 | — | 100 | 23.6 ± 2.5 |
| HSP70 | 2140 ± 483* | 59.3 | 78* | 14.7 ± 1.6 |
| HSP70-Fc | 1645 ± 546* | 84.9 | 67* | 11.4 ± 1.8 |
| $^{131}$I-HSP70 | 162 ± 49* | 98.7 | 59* | 7.6 ± 2.0 |
| $^{131}$I-HSP70-Fc | 119 ± 27* | 131.4 | 44* | 4.9 ± 2.2 |

*p > 0.05 compared to control;
**AUC for the tumor growth kinetics curve

Example 12

Application of the HSP70-Fc Fusion Protein for Treatment of Liver Fibrosis

We tested HSP70-Fc fusion protein that naturally accumulates in the liver for treating liver fibrosis in the mouse model of the liver fibrosis as described in the literature (T. Fujii, B. C. Fuchs, S. Yamada, G. Y. Lauwers, Y. Kulu, J. M. Goodwin, M. Lanuti K. K. Tanabe. Mouse model of carbon tetrachloride induced liver fibrosis: Histopathological changes and expression of CD133 and epidermal growth factor, Gastroenterology, 2010 (10)79). Specifically, 20 strain A/J male mice at approximately 5 weeks of age were purchased from Jackson Laboratory (Bar Harbor, Me.) and treated three times a week for 17 weeks with 0.04 cc of a 40 percent solution of $CCl_4$ (Sigma, St. Louis, Mo.) in olive oil. Administration of $CCl_4$ caused a moderate to severe liver injury as demonstrated by the development of severe liver damage with thick fibrotic septa and pseudolobular formation as well as serologically elevated levels of alanine transaminase (ALT) and aspartate transaminase (AST).

The animals were split in two groups of 10. One group served as control and received bolus injections of PBS whereas a treated group received 6 injection of HSP70-Fc fusion protein (50 microgram, IP) twice a week for 3 weeks. All animals were sacrificed at the end of the 4th week after beginning of the treatment. Treatment with HSP70-Fc resulted in attenuation of both histological (neuroinflammatory score going down from 2.9 to 1.2) and functional injury, with ALT levels dropping from 138±19 to 72±16 U/l and AST, from 188±25 to 95±21 U/l.

REFERENCES

Jammes Y, Steinberg J G, Delliaux S, Bregeon F, Chronic Fatigue Syndrome Combines Increased Exercise-Induced Oxidative Stress And Reduced Cytokine and HSP Responses. J. Intern. Med. 2009, 266(2), 196-206.

Lee C E, McArdle A, Griffiths R D The role of hormones, cytokines and heat shock proteins during age-related muscle loss. Clin. Nutr. 2007, 26(5):524-34

Maglara A A, Vasilaki A, Jackson M J, McArdle A, Damage to Developing Mouse Skeletal Muscle Myotubes in Culture: Protective Effect of Heat Shock Proteins. J. Physiol. 2003, 548(3)837-846.

Morton J P, Kayani A C, McArdle A, Drust B, Exercise-Induced Stress Response of Skeletal Muscle, with Specific Emphasis on Humans. Sport Med. 2009, 39(8), 643-662.

Panossian A, Wikman G, Evidence-Based Efficacy of Adaptogens in Fatigue, and Molecular Mechanisms Related to Their Stress-Protective Activity. Curr. Clin. Pharmacol. 2009, 4(3)198-219.

Slepian M J, Massia S P, Treatment of Tissues to Reduce Subsequent Response to Injury. U.S. Pat. No. 5,914,345.

Srivastava P K, Chandawarkar R Y, Compositions and Methods for Promoting Tissue Repair Using Heat Shock Proteins. US Patent Application US 2003/0012793.

Takahashi N., Heat Shock Protein Inducer. U.S. Pat. No. 6,846,845 B2.

Vígh L, Literáti P N, Horváth I, Török Z, Balogh G, Glatz A, Kovács E, Boros I, Ferdinándy P, Farkas B, Jaszlits L, Jednákovits A, Korányi L, Maresca B. Bimoclomol: a Nontoxic, Hydroxylamine Derivative with Stress Protein-Inducing Activity and Cytoprotective Effect. Nature Medicine, 1997, 3(10), 1150-1154.

Whitham M, Fortes M B, Heat Shock Protein 72: Release and Biological Significance Front. Biosci. 2008, 13, 1328-1339.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. An HSP70 fusion protein comprising (i) a first HSP70 domain fused to (ii) a second Fc domain, wherein the first and second domains are optionally linked by a third linker domain, wherein the HSP70 fusion protein is SEQ ID NO: 1.

2. The HSP70 fusion protein of claim 1, wherein the HSP70 domain is pegylated HSP70.

3. The HSP70 fusion protein of claim 1, wherein the HSP70 fusion protein is labeled with one or more radioactive isotopes.

4. The HSP70 fusion protein of claim 3, wherein the radioactive isotope is selected from the group consisting of I-123, I-124, I-125 and I-131.

5. A pharmaceutical composition comprising an HSP70 fusion protein, wherein the HSP70 fusion protein comprises (i) a first HSP70 domain fused to (ii) a second Fc domain, wherein the first and second domains are optionally linked by a third linker domain, and pharmaceutically acceptable carrier, wherein the HSP70 fusion protein is SEQ ID NO: 1.

6. The pharmaceutical composition of claim 5, wherein the HSP70 fusion protein is labeled with one or more radioactive isotopes.

7. The pharmaceutical composition of claim 6, wherein the radioactive isotope is selected from the group consisting of I-123, I-124, I-125 and I-131.

8. The pharmaceutical composition of claim 5, wherein the HSP70 domain is pegylated HSP70.

* * * * *